(12) United States Patent
Kurahashi et al.

(10) Patent No.: US 11,957,905 B2
(45) Date of Patent: Apr. 16, 2024

(54) ELECTRIC CURRENT STIMULATION DEVICE

(71) Applicant: ITO CO., LTD., Tokyo (JP)

(72) Inventors: Tsukasa Kurahashi, Tokyo (JP); Mayuko Kurahashi, Tokyo (JP); Daigo Yoshida, Tokyo (JP)

(73) Assignee: ITO CO., LTD., Tokyo (JP)

( * ) Notice: Subject to any disclaimer, the term of this patent is extended or adjusted under 35 U.S.C. 154(b) by 0 days.

(21) Appl. No.: 16/632,346

(22) PCT Filed: Jul. 25, 2018

(86) PCT No.: PCT/JP2018/027870
§ 371 (c)(1),
(2) Date: Jan. 18, 2020

(87) PCT Pub. No.: WO2019/022127
PCT Pub. Date: Jan. 31, 2019

(65) Prior Publication Data
US 2020/0206500 A1    Jul. 2, 2020

(30) Foreign Application Priority Data

Jul. 25, 2017  (JP) ................................ 2017-143143

(51) Int. Cl.
*A61N 1/36* (2006.01)
(52) U.S. Cl.
CPC ....... *A61N 1/36003* (2013.01); *A61N 1/3603* (2017.08)

(58) Field of Classification Search
CPC .... A61N 1/0408; A61N 1/0484; A61N 1/321; A61N 1/36; A61N 1/36003; A61N 1/3603; A61N 1/36034
(Continued)

(56) References Cited

U.S. PATENT DOCUMENTS 8,290,581 B2   10/2012  Kriksunov et al.
8,784,460 B2    7/2014  Kriksunov et al.
(Continued)

FOREIGN PATENT DOCUMENTS

CN     101878053 A    11/2010
JP    2007-054329 A     3/2007
(Continued)

OTHER PUBLICATIONS

Vinod Edward, EP Search Report issued in EP patent application No. 18838874.8, European Patent Office, dated Apr. 14, 2021, 5 pages.
(Continued)

*Primary Examiner* — Carl H Layno
*Assistant Examiner* — Jane C Kalinock
(74) *Attorney, Agent, or Firm* — ASLAN LAW, P.C.

(57) ABSTRACT

An electric current stimulation device includes a first electrode and a second electrode that are arranged in a body, and an output circuit that outputs an electric signal; wherein the electric signal by which the user feels no pain is output from the output circuit, and the electric signal is applied to a distal portion of extremities or near the same by the first electrode and the second electrode when arranging the body at the distal portion of the extremities of the user or near the same.

8 Claims, 19 Drawing Sheets

(58) Field of Classification Search
USPC .......................................................... 607/48
See application file for complete search history.

(56) References Cited

U.S. PATENT DOCUMENTS

| | | | |
|---|---|---|---|
| 9,433,773 B2 | 9/2016 | Chao et al. | |
| 10,092,762 B2* | 10/2018 | Jiang | A61N 1/37247 |
| 2007/0293911 A1* | 12/2007 | Crowe | A61N 1/36003 |
| | | | 607/48 |
| 2009/0112283 A1 | 4/2009 | Kriksunov et al. | |
| 2013/0013028 A1 | 1/2013 | Kriksunov et al. | |
| 2014/0155799 A1* | 6/2014 | Skahan | A61N 1/37247 |
| | | | 602/26 |
| 2015/0258327 A1 | 9/2015 | Chao et al. | |
| 2015/0321000 A1* | 11/2015 | Rosenbluth | A61N 1/0492 |
| | | | 607/48 |
| 2019/0167973 A1* | 6/2019 | Pisarev | A61B 5/11 |

FOREIGN PATENT DOCUMENTS

| | | |
|---|---|---|
| JP | 2013-501156 A | 1/2013 |
| JP | 2013-252386 A | 12/2013 |
| JP | 2016-202445 A | 12/2016 |
| KR | 10-2012-0099925 A | 9/2012 |
| WO | WO 2009/137683 A2 | 11/2009 |

OTHER PUBLICATIONS

Michelle H. Cameron, "Physical Agents in Rehabilitation From Research to Practice" EBM Butsuri Ryouhou Gencho 2nd Edition (Ishiyaku Pub, Inc.), 14 pages including p. 242 and written in 2003 and published the second edition in Japanese on Jan. 20, 2006.
The State Intellectual Property Office of People's Republic of China, Chinese Office Action issued in Chinese patent application No. 201880049581.4, China, dated Feb. 11, 2023, 6 pages.
Intellectual Property Office of Vietnam, Office Action issued in VN patent application No. 1-2020-00984, Japan, dated Dec. 20, 2022, 1 page.
Japanese Patent Office, JP Office Action (non-final) issued in JP patent application No. 2019-532829, dated Jul. 26, 2022, 4 pages.
Japanese Patent Office, JP Office Action issued in JP patent application No. 2019-532829, Japan, dated Dec. 20, 2022, 3 pages.
CN Office Action issued in CN patent application No. 201880049581.4, The State Intellectual Property Office of People's Republic of China, People's Republic of China, Nov. 27, 2023, 5 pages.

* cited by examiner

ELECTRIC CURRENT STIMULATION DEVICE

CROSS-REFERENCE TO RELATED APPLICATIONS

This application claims priority to JP Patent Application No. 2017-143143 filed on Jul. 25, 2017, and to PCT Application No. PCT/JP2018/027870 filed on Jul. 25, 2018, the entire contents of which are hereby incorporated by reference.

TECHNICAL FIELD

The present invention relates to a method of applying an electric signal for electric current stimulation of performing transcutaneous stimulation by electric current, to specifically a distal portion of extremities or near the same; and relates to an electric current stimulation device thereof.

BACKGROUND ART

A technique of applying an electric signal to a human body has been put to practical use. Most commonly, known has been a device for improving a muscle output by contracting muscles, as a transcutaneous stimulation device using electric current. This is the device of contracting the muscles or releasing the contraction thereof via electrical stimulation from the outside to effectively perform muscle training. The device significantly strengthens the muscles and improves the muscle output by restoring damaged muscle fibers as a stronger muscle tissue after damaging the muscle fibers microscopically and temporarily via application of a strong load to the muscle tissue to improve a physical motor function. On the other hand, for example, proposed is a technique of temporarily improving or lowering a muscle output by applying characteristic mild electric current to muscles as disclosed in Patent Document 1.

PRIOR ART DOCUMENT

Patent Document

Patent Document 1: Japanese Unexamined Patent Application Publication No. 2016-202445

SUMMARY OF THE INVENTION

Problems to be Solved by the Invention

The above-described method effectively performs muscle training by contracting muscles via strong electric current stimulation to largely grow/powerfully strengthen the muscles. As a result of this, a muscle output is improved, but the muscle output cannot be improved to such an extent that a muscle tissue is largely grown. Further, according to relaxing of the muscles, there is only a method of eventually obtaining relaxation of the muscles by repeating contraction of the muscles and releasing of the contraction thereof, and thus a conventional electric current stimulation device has not been able to directly perform relaxing of the muscles.

On the other hand, according to the above-described Patent Document 1, it is made possible to perform muscle strength improvement and relaxing of a specific muscle by arranging a pair of conductors along the specific muscle as an object to apply electrical stimulation for which ramp-up or ramp-down time is controlled thereto.

However, those obtaining actuations are limited to a specific muscle to which electrical stimulation is applied by arranging electrodes, and thus no effect with respect to a large number of muscles at one time could be obtained, and no action such as tension and releasing of the muscles or the like could be simultaneously applied to a plurality of the muscles.

Means to Solve the Problems (1) In order to solve the above-described problem, the present invention has implemented the following means. That is, it is a feature that an electric current stimulation device according to the present invention comprises a first electrode and a second electrode that are arranged in a body, and an output circuit that outputs an electric signal; wherein the electric signal by which the user feels no pain is output from the output circuit, and the electric signal is applied to a distal portion of extremities or near the same by the first electrode and the second electrode when arranging the body at the distal portion of the extremities of the user or near the same.

(2) Further, it is a feature that an electric current stimulation device according to the present invention comprises a first electrode and a second electrode that are arranged at a position with which a distal portion of extremities of a user or near the same comes into contact, wherein an electric signal that is not felt by the user is supplied to the distal portion of the extremities or near the same by the first electrode and the second electrode.

(3) Further, it is a feature that an electric current stimulation device according to the present invention is a device used by the user, comprising the electric current stimulation device according to the foregoing (2).

Effect of the Invention

According to the present invention, provided can be an electric current stimulation device capable of giving tension or releasing of the tension, or the other effect to a whole body by applying mild electric current stimulation to a distal portion of extremities or near the same.

DETAILED DESCRIPTION OF EMBODIMENTS

Embodiment 1

Figure 1A:
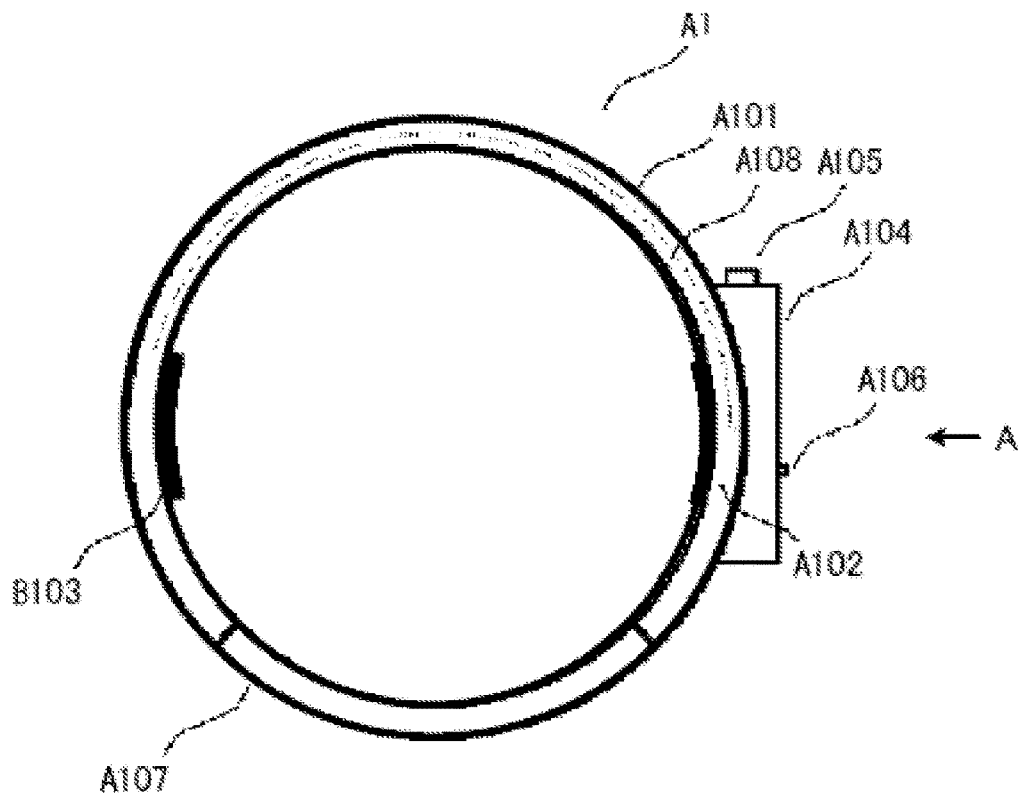
FIG. 1 is an explanatory diagram of a body A1 according to the present invention.

FIG. 1(a) shows an appearance side face of a body A1 of an electric current stimulation device according to the present invention. The body A1 comprises a belt part A101, a stretchable part A107, and a controller A104. An electrode A102 as a first electrode and an electrode B103 as a second electrode that come into contact with a human body are arranged on the belt part A101, and these electrodes are connected to the controller A104 by a harness A108 arranged inside the belt A101. Since the harness A108 is not seen from outside, only its position is shown with a dotted line. The same figure (b) is a front view obtained by viewing the body A1 from a direction of an arrow A in the same figure (a).

The stretchable part A107 made of silicone rubber, for example, is easy to be stretched; and the body part is worn around extremities, for example, a wrist via stretching of the stretchable part A107. In the wearing state, the electrode A102 and the electrode B103 are brought into contact with skin of the wrist, and the after-mentioned electrical stimulation can be applied thereto. The portion around which the body A1 is worn is not limited to the wrist, but may be an ankle, and wearing around a distal portion of the extremities or near the same is preferable. Specifically, as to ease of wearing in addition to its being hard to be detached, handing during use, and so forth, it is easy to be worn around the wrist or the ankle. The present embodiment will be explained such that the body A1 is worn around the wrist. The stretchable part A107 is not limited to a silicone rubber, but can also be made of natural rubber or urethane rubber.

The body A1 is worn in such a manner that the controller A104 is on the back side of a hand around a wrist, and the electrode A102 and the electrode B103 come into contact with the back side of the hand around the wrist and the palm side of the hand around the wrist, respectively. In addition, in contrast, the controller A104 is worn so as to be on the palm side of the hand, and the electrode A102 and the electrode B103 may come into contact with the palm side of the hand around the wrist and the back side of the hand around the wrist, respectively.

The body A1 is formed from the belt part A101 and the stretchable part A107 in an annular shape, but the belt part A101 is made to be formed of silicone rubber, natural rubber or the like in an annular shape, and thus it may be so constituted that the body A1 can be worn around a wrist or the like by stretching of the entire belt part. Herein, the annular shape may not be a circle, but may be for example, an ellipse, a triangle, or a polygon such as a rectangle or the like, and even though being in a shape other than the foregoing, it is good enough to be appropriately worn around the wrist.

The belt part is made to be belt-shaped so as not to be an endlessly annular shape and fixing means such as a surface fastener, a button, a hook or the like may be attached to both end portions, and for example, it is good enough to be such a configuration as making an annular shape by being wound around the wrist to be fixed with the surface fastener. Alternatively, it is good enough to be such a configuration as having an open end without having an endless shape even when wearing, for example, that attaching/detaching is made to be facilitated by elasticity of the plate spring, and the skin and the electrode are easily and surely made to be brought into contact with each other by constituting the belt-shaped belt part whose part becomes an open end, using an elastic plate spring.

The electrode A102 and the electrode B103 each are formed from solid gel exhibiting high conductivity or low electrical resistance, for example. However, without limitation to this, the electrode fits the portion around which the body A1 is worn, from which an electric signal may be able to be appropriately applied to skin, and may be formed from metal such as a molded stainless plate or the like, or formed from conductive cloth in which silver thread or the like is used, or formed from a conductive paint. Alternatively, rubber exhibiting conductivity is good enough, for example, usable is conductive rubber that is made to exhibit conductivity by mixing a conductive material typified by carbon powder as silicone rubber or urethane rubber.

The controller A104 is provided with a switch A105 and LED-A106, and an electric signal applied to the electrode A102 and the electrode B103 can be controlled. LED-A106 is lit when pushing the switch A105, and the after-mentioned electrical stimulation is supplied near a distal portion of extremities via the electrode A102 and the electrode B103, or to a wrist according to the present embodiment.

Figure 2:
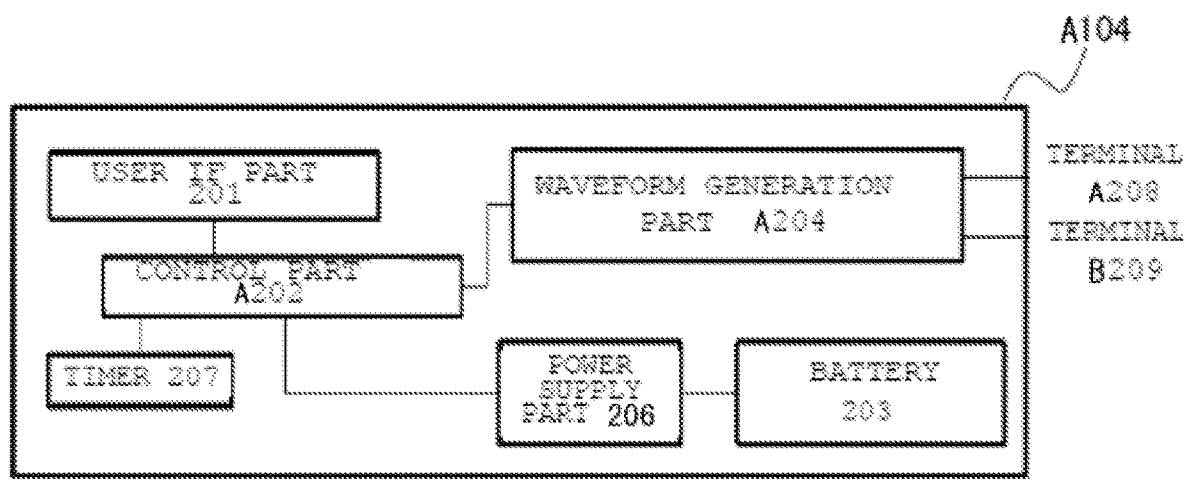
FIG. 2 is a block diagram of a controller according to the present invention.

"FIG. 2 shows a block diagram of a controller A104. The controller A104 is constituted to include at least part or all of a control part A202 that controls the electrical signal, a waveform generation part A204 that is an output circuit, a timer 207, a user IF part 201, a power supply part 205, a battery 203 and so forth. The present embodiment will be explained such that the controller A104 is constituted from all of these."

The control part A202 incorporating an interface part for connecting to each part in addition to CPU and a memory is connected to the waveform generation part A204 that generates an electric signal providing electric current stimulation, the timer 207 for managing an output during a fixed time, and the user IF part 201 connected to the switch A105 and LED-A106; and controls the foregoing.

Power supplied from the battery 203 is supplied to each part via the control part A202 by being controlled to a predetermined constant voltage value, for example, 5 V by the power supply part 206.

When pushing the switch A105 after a user wears the body A1 around a wrist, the information is sent to the control part A202 via the user IF part 201, and the control part A202 gives an instruction to the waveform generation part A204 so as to output the after-mentioned electric signal. Alternatively, the control part A202 may have such a configuration as making the waveform generation part A204 start generating the electric signal by supplying power to the waveform generation part A204.

The control part A202 supplies parameters of the generated electric signal to the waveform generation part A204 via readout from a memory that constitutes the control part A202 or that is provided outside the control part A202, and the waveform generation part A204 may output the electric signal in accordance with the parameters.

The electric signal output by the waveform generation part A204 is supplied to the electrode A102 connected to a terminal A208 by a harness A108 and the electrode B103 connected to a terminal B209 by the harness A108. The timer 207 starts measuring a predetermined time, for example, 15 minutes or one hour by instructing the time measurement to the timer 207 synchronously with instructing the output to the waveform generation part A204. Information about the measurement of the timer 207, for example, the information at the time when a predetermined time elapses is fed back to the control part A202, and when the control part A202 instructs generation stop of the electric signal to the waveform generation part A204, or stops power supply to the waveform generation part A204 via the feedback, the output of the electric signal is stopped.

The control part A202 gives an instruction to the user IF part 201 so as to light LED-A106, in accordance with the power supply to the waveform generation part A204; and the user IF part 201 lights LED-A106 by supplying power to LED-A106. In contrast, when the control part A202 stops power supply to the waveform generation part A204, or instructs generation stop of the electric signal, an instruction is given to the user IF part 201 so as to turn off LED-A106, and the user IF part 201 turns off LED-A106 by stopping the power supply to LED-A106.

According to the battery 203, a battery having relatively small capacity is usable since the body A1 uses mild electric current, and may be for example, a button type battery. Alternatively, it may be good enough to be a battery that is repeatedly usable via charging as in the case of a lithium ion battery. Alternatively, it may be good enough to be such a configuration as being usable by connecting to a DC power supply for which a home outlet is used in place of the battery 203.

FIG. 3 schematically shows electric signals supplied to extremities according to the present invention. In FIG. 3, the horizontal axis represents time, and the vertical axis represents electric current values. When a set of a plurality of pulses is referred to as a pulse group, as seen in FIG. 3(a), according to the present embodiment, a second pulse group formed from a plurality of pulses having a fixed amplitude is used and the second pulse group is output again after lapse of time (T4) when no electric signal is output, and this is repeated. In addition, in FIG. 3, the vertical axis represents electric current values, and in the present specification, the amplitude is used as wording that means an amplitude of an electric current value, but the present invention is not limited thereto; the amplitude also means an amplitude of the electric current value, the voltage value or the power with regard to pulses; and further, the amplitude is not limited to an amplitude of the electric current or the voltage, or of the power.

In addition, the above-described second pulse group is output as an example at a frequency of 50 Hz, a pulse width of 200 μsec, and an output of 50 μA. Thus, a larger number of pulses than that of pulses described in the figure is actually applied thereto, but a part thereof is used and described for simplification, in order to clearly explain the pulse group.

An output (hereinafter, referred to as "insensitivity output") with which a human body cannot sense electrical stimulation is used for pulses according to the present embodiment. In general, pain caused by electric current is easy to be generated when exceeding an electric current value of 20 mA. As is read from FIGS. 8 to 20 of EBM Butsuri Ryouhou Gencho 2nd Edition (Ishiyaku Pub, Inc.) at page 242, an output of 20 mA or more is required for causing muscle contraction, but in contrast, when being 20 mA or less, the muscle contraction is hardly generated even though it is felt that the electric signal is applied thereto. Further, as in the case of the present example, the muscle contraction not only is not caused by setting approximately 50 μA but conventionally, a person is neither able to feel that the electric signal is supplied thereto, nor feels pain caused by the electric signal, unless a special condition is met.

According to the present invention, the effect on a whole body is produced by applying the above-described electric signal to a distal portion of extremities or near the same, only using a set of electrodes, and the tension-relaxing effect on the whole body is specifically produced. As described above, a set of electrodes A102 and B103 are arranged on a palm side of a hand around a wrist, and a back side of the hand around the wrist. According to the prior art, the effect is limited to muscles existing at the portion where the electrodes are attached, but according to the present invention, neither nerves nor muscles along the arrangement of these electrode are present around the portion where the electrodes are attached, that is, around a wrist are not present, and there is no action produced due to special nerve and muscle stimulation caused by the applied electric signal. According to the present invention, the effect specific to the present invention is produced in such a manner that the tension-relaxing effect on the whole body is produced by applying the electric signal to a distal portion of extremities or near the same. Further, it becomes clear that the effect is maintained for a long period of time even after stopping electric signal supply, and this maintainability is also the effect specific to the present invention.

From those described above, a very comfortably relaxed feeling can be obtained by acquiring tension relaxation over a whole body according to the present embodiment. Accordingly, in the case of the use after exercise, more effective cooling-down and fatigue recovery can be preferably expected, or in the case of the use before going to bed as well, not only a mentally relaxed feeling but also good sleep is preferably obtained by relaxing the whole body.

Embodiment 2

Figure 3A:
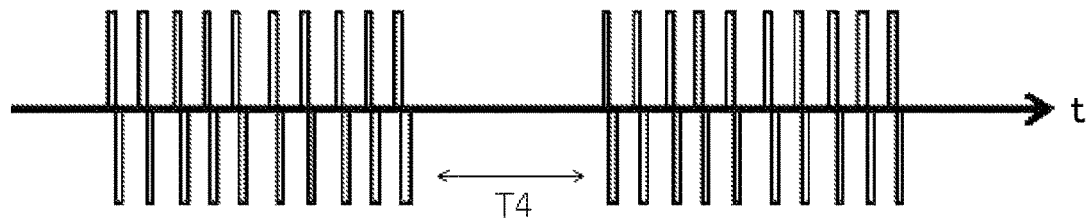
FIG. 3 is a schematic diagram of output waveforms according to the present invention.
Figure 3B:
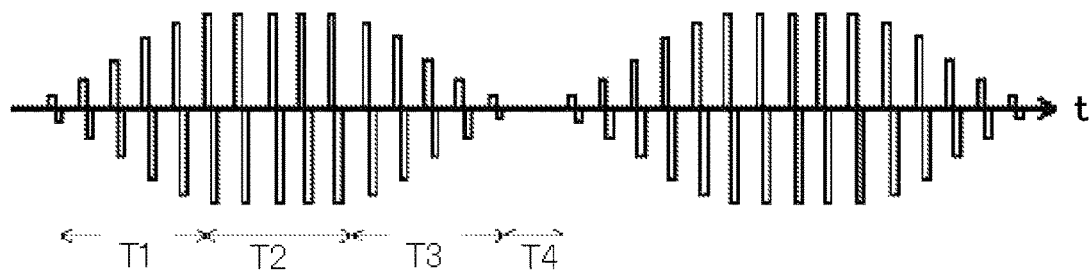
Figure 3C:
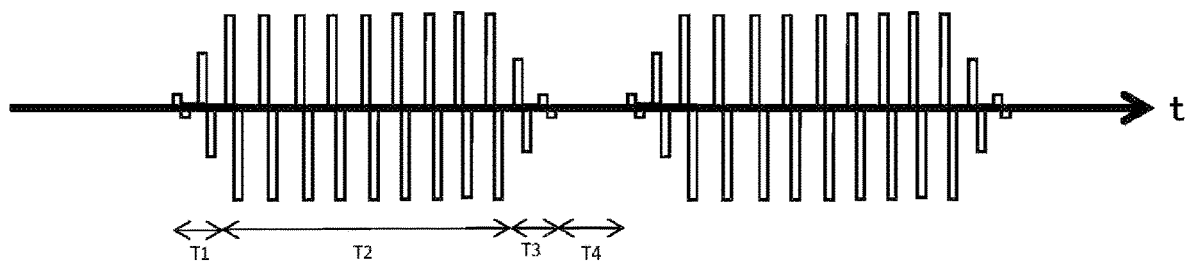
Figure 3D:
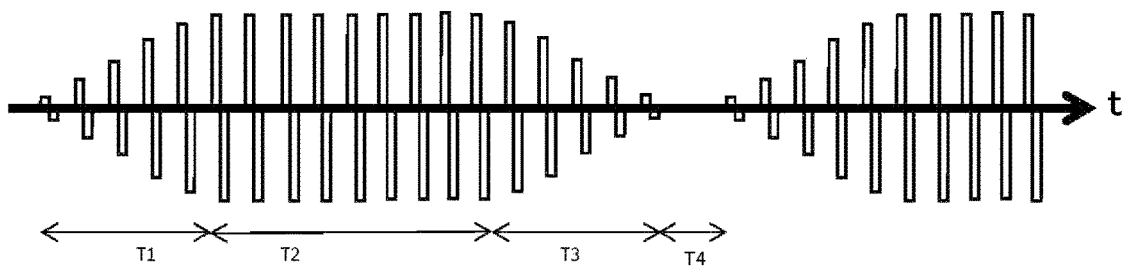

According to the present embodiment, those concerning application of the electrical stimulation to a wrist as a distal portion of extremities are identical to the above-described whole body A1, but the electric signal as shown in FIG. 3(b) is specifically used by making the applied electric signal different. This electric signal is constituted from a plurality of pulse groups. Specifically, the electric signal according to the present embodiment is formed from a first pulse group in which the output is gradually increased, a second pulse group in which the fixed output is maintained, and a third pulse group in which the output is gradually lowered. In other words, the first pulse group may be said to be a pulse group in which an amplitude of each pulse constituting the pulse group gradually becomes large, or may be said to be a pulse group including at least a first pulse with a first output, and a pulse output after the first pulse by an output that is not smaller than the first output or a pulse group including at least the first pulse with a first amplitude, and a pulse output after the first pulse by an amplitude larger than the first amplitude. The second pulse group may be said to be a pulse group in which an amplitude of a plurality of pulse groups is fixed in the second pulse group, or may be said to be a pulse group constituted by a plurality of pulses with a second output or a pulse group constituted by a plurality of pulses with a second amplitude. The third pulse group may be said to be a pulse group in which an amplitude of each pulse constituting the pulse group gradually becomes small, or may be said to be a pulse group including at least a third pulse with a third output, and a pulse output after the third pulse by an output that is not larger than the third output or a pulse group including at least the third pulse with a third amplitude and a pulse output after the third pulse by an amplitude smaller than the third amplitude. Further, a pulse group constituted from the first pulse group, the second pulse group, and the third pulse group is referred to as a fourth pulse group. The fourth pulse group is repeated at fixed time intervals in a predetermined time, for example, one hour. Herein, the continuation time of the first pulse group is represented by T1; the continuation time of the second pulse group is represented by T2; the continuation time of the third pulse group is represented by T3, and T4 represents the rest time of the fourth pulse group, that is, a time interval until the output of the first pulse group is restarted after finishing the output of the third pulse group. The present embodiment is used for applications other than the foregoing embodiment 1 by using the first pulse group and the third pulse group in combination.

Figure 4:
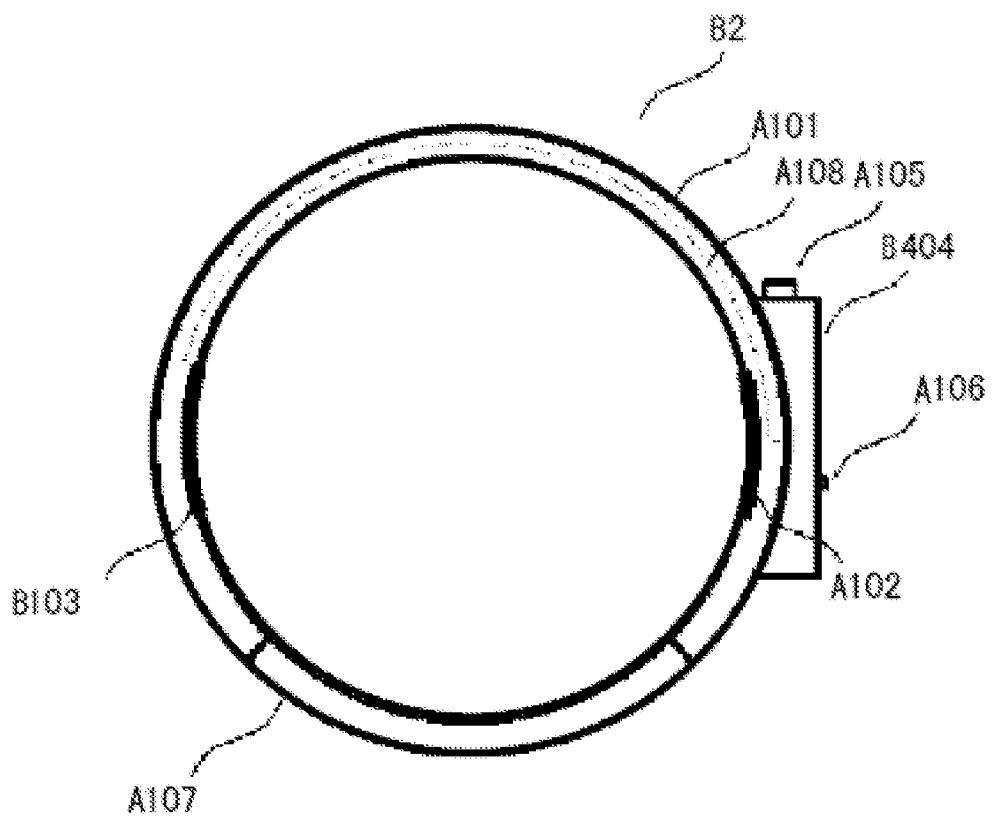
FIG. 4 is an explanatory diagram of a body B2 according to the present invention.

FIG. 4 shows a body B2 according to the present embodiment. The body B2 is substantially the same as the body A1, and thus the front view is omitted. With regard to the same symbols as in the body A1, those that are identical to symbols in the body A1 are applied thereto, and thus the explanation will be omitted. The body B2 differs from the body A1 in that a controller B404 is used.

Figure 5:
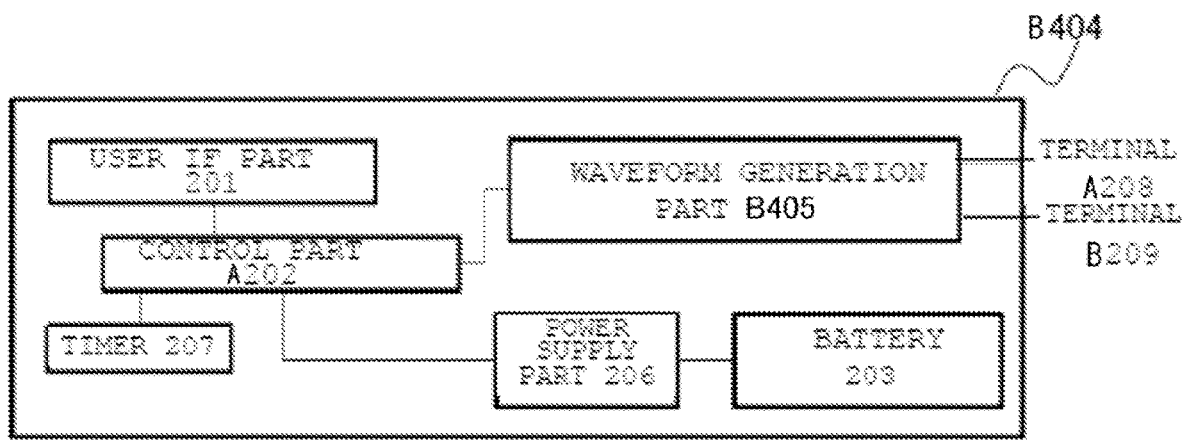
FIG. 5 is a block diagram of a controller according to the present invention.

FIG. 5 is a block diagram of a controller B404. For the controller B404 with respect to the controller A104, a waveform generation part B405 is only different therefrom, the explanation other than this will be omitted. The waveform generation part B405 outputs the electric signal as shown in FIG. 3($b$). According to the present embodiment, T1, T2, and T3 are set to 1.8 seconds, 3 seconds, and 1.8 seconds, respectively. Parameters concerning the electric signal other than this, such as a frequency, a pulse width, an electric current value and so forth may be identical to those of the body A1. Thus, a larger number of pulses than that of pulses described in the figure is actually applied thereto, but only a part thereof is used and schematically described for simplification, in order to clearly explain the pulse group.

In addition, a series of parameters may be applied to each pulse group, but a different parameter may be applied to each pulse group. For example, the frequency and the pulse width may be controlled so as to be different in each pulse group from each other. Alternatively, the parameters, for example, a frequency, an amplitude, a pulse width and so forth may be changed by the unit of the fourth pulse group.

According to the body B2, T1 and T3 each are set to 1.8 seconds that are not less than 1.5 seconds. The tension effect on a whole body is produced by applying such an electrical stimulation, that is, a pulse group of T1 and T3 each set to 1 second or more, 1.2 seconds or more when the more stable effect starts to be produced, and preferably 1.5 seconds when the effect tends to be highly and surely produced, for example, of T1 and T3 each set to 1.8 seconds to a distal portion of extremities or near the same. As described above, according to the present invention, there is very little to no muscle according to electric current caused by an electric signal supplied to a distal portion of extremities or near the same by a set of the electrodes A102 and B103 and further, no muscle contraction is generated, and thus it is clear that a different effect that is not the effect caused by stimulation of the contraction of specific muscles via applied electric signal is produced. According to the present invention, the effect specific to the present invention is produced such that the tension effect on the whole body is produced by applying the electrical stimulation to a distal portion of extremities or near the same. Further, it becomes clear that the effect is maintained for a long period of time even after stopping electric signal supply, and this maintainability is also the effect specific to the present invention.

From those described above, a very comfortable tension feeling can be obtained by acquiring tension relaxation over a whole body according to the present embodiment, and a refreshed feeling can also be obtained by the tension feeling. Accordingly, it is effective to be used at or immediately before a wakeup time in the morning, during fatigue, before starting exercise, during driving, before starting studying, and during studying.

The present invention is not limited to the above-described embodiments. Next, a modified example of each embodiment as described above is shown as another embodiment. However, the present invention is not limited thereto, and thus the following modified example may be used by combining the body A1 and the body B2 as described above and at least two of the following modified examples and the above-described embodiments 1 and 2 may be used in combination.

Figure 6:
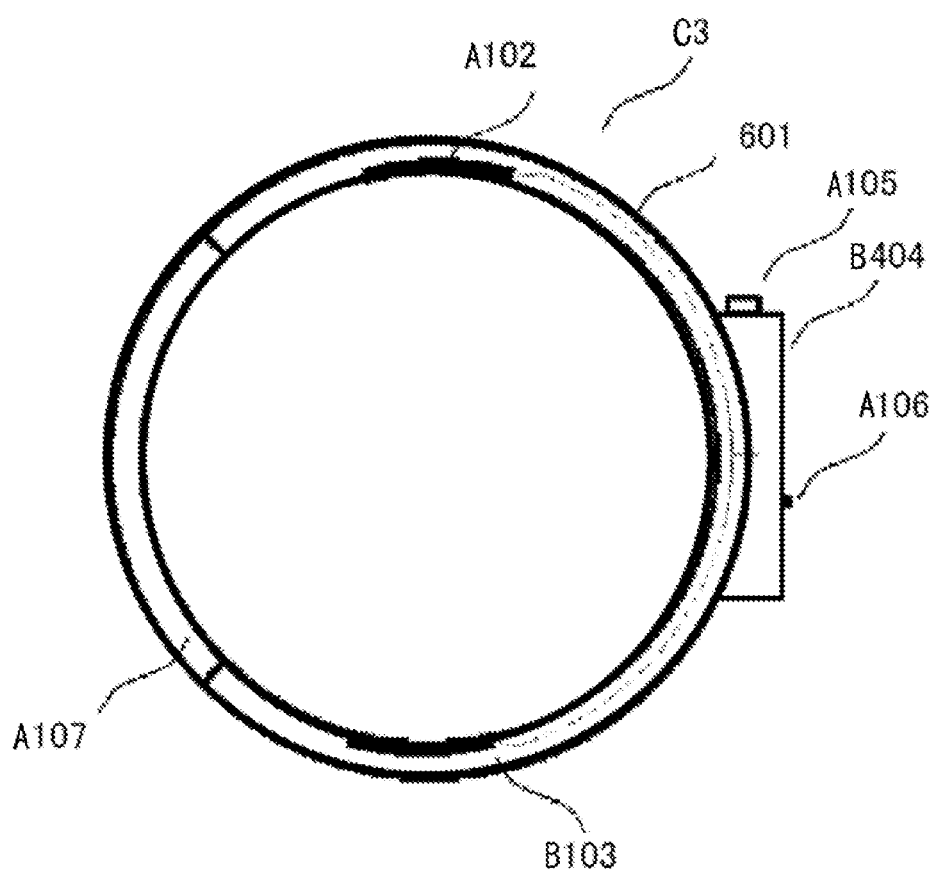
FIG. 6 is an explanatory diagram of another example according to the present invention.

FIG. 6 shows a body C3 as a modified example. The body A1, the body B2, or the like as described above is worn so that the controller A104 and the controller B404 each are attached onto the back side or the palm side of a hand around a wrist, and thus the electrode A102 and the electrode B103 are also on the back side or the palm side of the hand around the wrist. The electrodes A102 and B103 are not on the back side or the palm side of the hand around the wrist, but may be arranged on the right and left sides toward the back and palm of the hand as in the case of the body C3 of FIG. 6, that is, may be arranged so as to sandwich the wrist from the right and left. Alternatively, they may be placed around the wrist side by side. For example, the electrodes A102 and B103 may be arranged side by side along a circumferential direction of the wrist at the belt part A101 so as to be adjacent to each other, but they may be arranged side by side in a direction perpendicular to the circumferential direction so as to be adjacent to each other, and may be arranged side by side obliquely to the circumferential direction. In this manner, as to the arrangement of the electrodes, the present invention is not aimed at the stimulation of specific points and muscle contraction directly caused by the electric signal, and thus according to the present invention, electrodes can be arranged irrespective of the muscle direction as well as the point position or irrespective of presence/absence of the muscle and the point, or irrespective of a muscle amount along an electric current passage. FIG. 6 shows a body C3 where electrode positions in the body B2 are changed as an example, but as to devices subjected to applying electric current to a distal portion of extremities or near the same according to the present invention, including the body A1, electrode positions may be made to be situated in this manner, and this is applicable to each body as after-mentioned.

Another modified example is shown. Each embodiment as described above is a configuration of being able to apply the second pulse group (hereinafter, referred to as "first signal") as shown in FIG. 3($a$) from an electric signal by which relaxation to a tension feeling is produced for a whole body, or the fourth pulse group (hereinafter, referred to as "second signal") as shown in FIG. 3($b$), with a single body; but without being limited thereto, it may be so constituted that both electric signals are output with a single body. In this case, it may be so constituted that the first signal, for example, is output by initially pushing a switch A105, for example, and the second signal is output by pushing the switch A105 again; and further, it may be so constituted that an output is stopped by pushing the switch A105. That is, it may be so constituted that signals are sequentially switched, or the output is stopped every time when pushing the switch A105.

It is not merely pressing to press the switch A105 but it may be so-called double click or long press, and an operating method may be used differently in such a manner that the double click is done when switching an output signal; the long press is done when starting or stopping the output signal; and so forth. According to such a configuration, malfunction of a device when touching the switch A105 by mistake can be preferably avoided.

Herein, in the case of changing the output signal, it may be so constituted that parameters of the first signal when pushing the switch A105, for example, or parameters of the second signal when pushing the switch A105 again, for example, are fed to an output circuit of the waveform generation part A204 or the like from the control part A202, and the output signal can output a signal such as the first signal, the second signal or the like in accordance with each of the parameters.

Another modified example is shown. The output of pulses used as described above is set to 50 μA, but without being limited thereto, may be for example, 40 ρA, 100 μA or the like. Alternatively, an output value may be adjusted so as to obtain a desired effect, for example, the output may be adjusted by making a part of controlling an operation of a body such as the controller A104, the controller B404 or the like have a volume function. The above-described effect is preferably one in which the output is adjustable, since there may be individual differences.

Another modified example is shown. According to the output of pulses used as described above, for example, the output used for the second pulse group uses one value at 50 μA, but the present invention is not limited thereto. The output values of the first signal and the second signal may be changed. For example, in the case of the first signal, a value of 50 μA is set, but in the case of the second signal, 100 μA may be set. Alternatively, as to the first signal and the second signal, the output value may be changed from 50 μA in a fourth pulse group unit. For example, immediately after pushing the switch A105, that is, an output of the second pulse group according to the initial fourth pulse group is 50 μA, but the output of the second pulse group according to the following fourth pulse group is set to 52 μA, and after this, the output value may be changed gradually in the fourth pulse unit. Alternatively, it may be so constituted that the output value is raised or lowered.

Another modified example is shown. According to the output of pulses used as described above, for example, the output used for the second pulse group is the above-described 50 μA, and thus an output with which a human body cannot sense electrical stimulation is used, but the preset invention is not limited thereto. According to an output (hereinafter, referred to as "felt output") capable of sensing the electrical stimulation around a wrist, and the output in the range where muscle contraction is not generated and no pain is felt via the electrical stimulation, for example, it may be roughly an output of 500 μA. Further, both the first signal and the second signal each may be set to a felt output, but at least one of them may be set to the felt output, and for example, it may be so constituted that the first signal is set to an unfelt output and the second signal is set to the felt output, or vice versa. This is able to more easily determine which signal of the first signal and the second signal is used by a user. As described above, no muscle contraction is generated by setting an electric current value of the electric signal to 20 mA or less, and pain is hardly felt by setting it to several mA or less. Of course, sensitivity to the pain depends on a place where the electric signal is fed, and individual differences, but it appears that most of people do not feel pain, if there is no wound around a wrist, by setting it to 500 μA as described above.

Another modified example is shown. According to the output of pulses used as described above, for example, the output used for the second pulse group uses a fixed output as described above, but the present invention is not limited thereto. It may be so constituted that immediately after starting an output, a felt output, for example, 500 μA is set as an output of the second pulse group; and after elapse of a fixed time from starting the output, for example, after the elapse of 30 seconds from starting the output, the output of the second pulse group is changed to an unfelt output, for example, 50 μA. The change of the output may be made to suddenly change, for example, from the felt output to the unfelt output, that is, from 500 μA to 50 μA; and may be controlled so as to finally become 50 μA by gradually changing from 500 μA to 400 μA, 300 μA, . . . . In addition, the felt output is very weak electric power to such an extent that no pain is felt as described above, thereby being usable as the second signal, and even though using the felt output that uses 500 μA thereof and the unfelt output in combination, the same effect as that of the unfelt output is produced when the output is relatively small or relatively in a short time as in the case of the felt output, and no effect caused by the unfelt output is inhibited. For example, there is neither malfunction nor adverse effect produced by using the felt output, in which the use of the felt output lowers the effect caused by the unfelt output, etc. Accordingly, it leads to more effectively producing the effect caused by the unfelt output in the following manner that the felt output is temporarily used.

According to the case of using the unfelt output, it cannot be known that no output is appropriately given because of the case of failing to push the switch A105 since a user cannot sense an output, a low remaining amount of the battery 203, or the like, and thus there appears a malfunction by which the user does not notice that no output is given. However, the user can easily know that an electric signal is output by using the felt output after starting an output as described above and in contrast, the user can easily know that no output is given when no felt electrical stimulation is obtained immediately after starting the output, and thus the malfunction can be easily avoided. For example, the improvement is easily made in such a manner that the operation is re-performed by easily noticing an incorrect switch operation and battery run-out; the battery 203 is replaced and charged; and so forth. Further, the user cannot feel electrical stimulation when only using the unfelt output, and thus there is a case of having our doubts about whether or not the electric signal is actually output, that is, the device is normally operated. However, since temporarily felt electrical stimulation exists, the user can easily know the normal operation of the device, and the effect can be improved by actually feeling the output.

The temporarily felt output as described above can be used not only immediately after starting the output but before ending the output. For example, the user can be notified of the output being about to end by changing to the felt output in place of the unfelt output from 30 minutes before the output ends. When using the unfelt output, there has been a problem such that the user cannot know when the output ends, but the felt output is used just before the end of output, and thus the user can easily know the end. In addition, allowed is changing from the unfelt output to the felt output, for example, suddenly from 50 μA to 500 μA when the unfelt output is 50 μA; and also allowed is controlling so as to finally become 500 μA by gradually changing from 50 μA to 100 μA, 200 μA, and 300 μA.

The temporarily felt output as described above can be used not only when starting or ending the output but when both starting and ending the output. Alternatively, the user can be notified of the device that is normally operated, together with the elapse of time by using the temporarily felt output on a regular basis. For example, the felt output may be used by the first signal or the second signal every time the output continues for 5 minutes. Further, when the user feels felt stimulation, whether the output ends, or merely shows the elapse of time can be more preferably determined easily by replacing the continuation time of the felt output used for when the output is subsequently given (when showing the elapse of time), with the continuation time of the felt output used for when the output ends.

The use of the felt output when starting and ending the output or in a short time on a regular basis, that is, the configuration in which the felt output is temporarily used, as described above, is more preferable in the following respect. The felt output makes a person feel no pain, but it is not always true that it does not give a stress to the person to feel this stimulation for a long time. Accordingly, although pain is made not to be felt by the felt output, the felt output stays preferably for the use in a short time, and in a temporary manner, and it is more preferable in terms of not giving a stress to a user that such a felt output is temporarily used in place of the unfelt output. As described above, when using the unfelt output, the felt output can be temporarily used as notification means for notifying the user of information such as starting and ending the output of the electric signal, the elapse of time, or the like Another modified example is shown. According to the above-described, the first signal is the output of only the second pulse group as shown in FIG. 3(a), but the present invention is not limited thereto. It is also possible to use the electric signal as shown in the same figure (b) as the first signal, that is, the fourth pulse group. However, in this case, T1 and T3 each are 1 second or less; 0.8 seconds or less when a stable effect starts to be obtained; or preferably 0.5 seconds or less when the tendency of more surely producing the effect is high. In this manner, the fourth pulse group is possible to be used as the first signal that is an electric signal with which relaxation of a tension feeling on a whole body is obtained by setting T1 and T3 each of the fourth pulse group to 1 second or less.

Figure 1B:
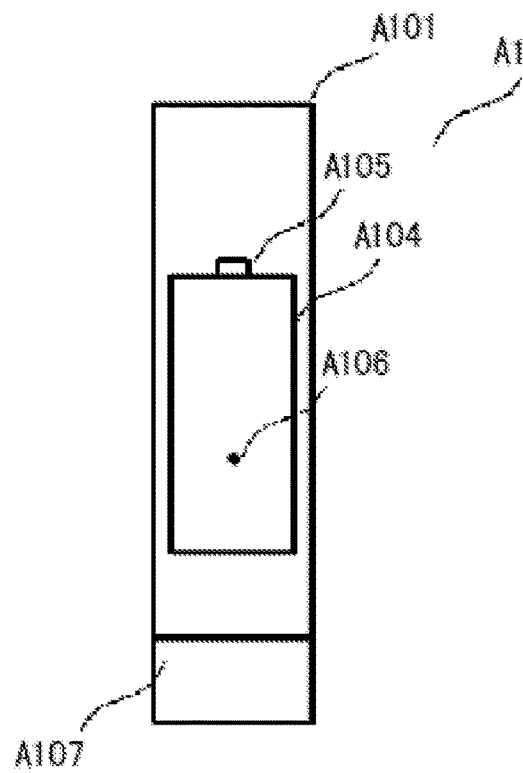

Another modified example is shown. According to the present invention, there may be a body F (The body F has the same appearance as that of the body A1 or the body B2, and thus the appearance of the body F is shown in FIG. 1 or FIG. 4) comprising a configuration capable of outputting the fourth pulse group in which T1 and T3 each are set to 1 second or less (for example, 0.3 seconds) as the first signal, or the fourth pulse group in which T1 and T3 each are set to 1 second or more (for example, 1.8 seconds) as the second signal.

In this case, for example, it may be so constituted that the fourth pulse group with 0.3 seconds as each of T1 and T3 is output as the first signal when initially pressing the switch A105, and the fourth pulse group with 1.8 seconds as each of T1 and T3 is output as the second signal when pressing the switch A105 again; and it may be so constituted that the output is stopped by further pushing the switch A105.

Figure 8:
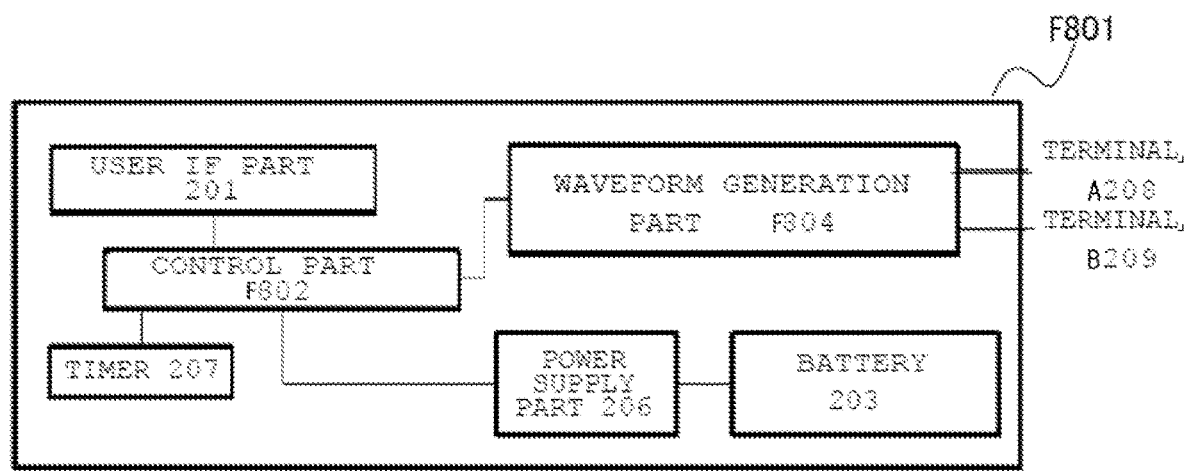
FIG. 8 is a block diagram of a controller according to the present invention.

When outputting the first signal and the second signal, the waveform generation part F804 capable of outputting both of them is used, and the controller F801 in which the waveform generation part F804 is used is shown in FIG. 8. As in the case of the waveform generation part F804, when generating the second signal can be adapted to a circuit configuration common to an outputting circuit even at the time when outputting the first signal by setting each of T1 and T3 to for example, 0.1 seconds or 0.3 seconds. That is, both the first signal and the second signal can be output by a single output circuit.

Originally, the first pulse group and the third pulse group each are aimed at reducing pain caused when large electric current in such an extent that muscle contraction is caused flows through muscles, and pain caused by the strong muscle contraction, but when there is wound, inflammation or the like on the skin even in the case of mild current by which the muscle contraction is less likely to be caused, pain as well as an unpleasant feeling caused when the electric current flows through not muscles but an affected area of the wound, the injury, or the like can also be reduced.

Alternatively, when there are the wound and inflammation on the skin, even in the case of the unfelt output, the unfelt output is able to act as the felt output by feeling applied electrical stimulation even if no pain is felt. Even in the case of feeling no pain as previously mentioned, it is not preferred that the felt stimulation is able to apply stress to a user. In this case, it becomes difficult to sense the fed electrical stimulation, even when there are the wound and inflammation on the user's skin, by using the above-described fourth pulse group as the first signal. Thus, the fourth pulse group is more preferably used as the first signal, and in this case, it is realistic that T1 and T3 each are 1 second or less and 0.1 seconds or more. A control part F802 is arranged in a controller F801, and it may be so constituted that the first signal or the second signal is output from a waveform generation F804 by notifying the waveform generation F804 of information indicating that T1 and T3 each are for example, 0.3 seconds when using the first signal, or of information indicating that T1 and T3 each are for example, 1.8 seconds when using the first signal.

Figure 7A:
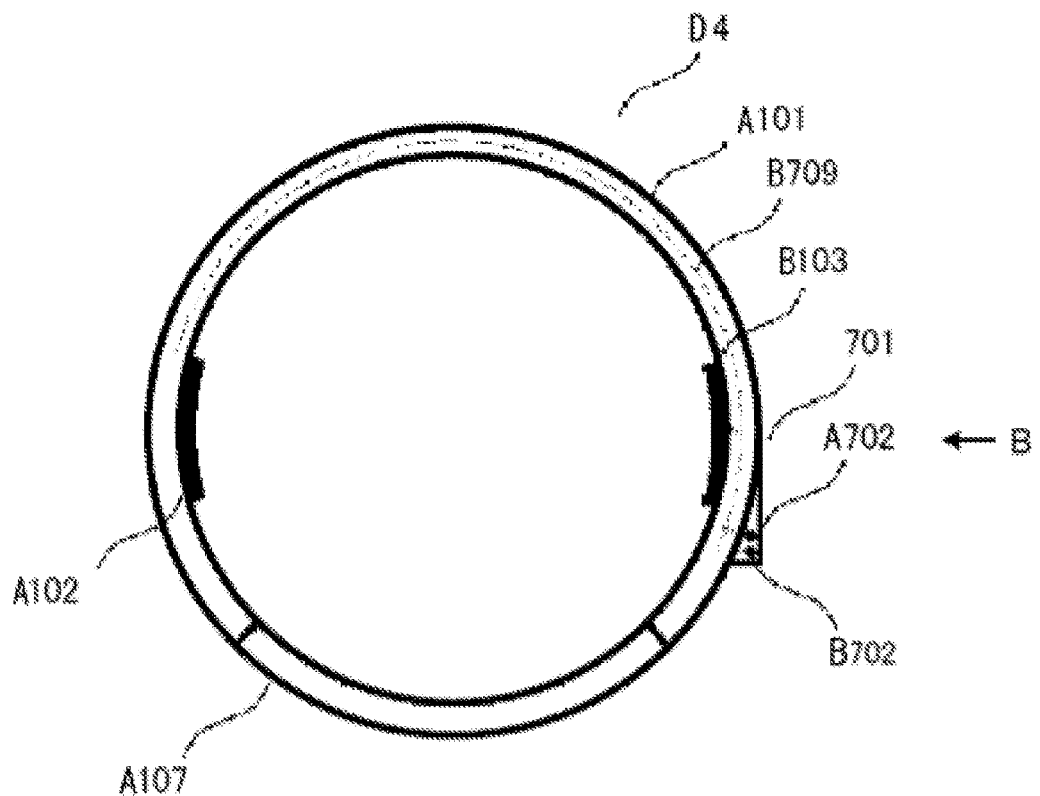
FIG. 7 is an explanatory diagram of another example according to the present invention.
Figure 7B:
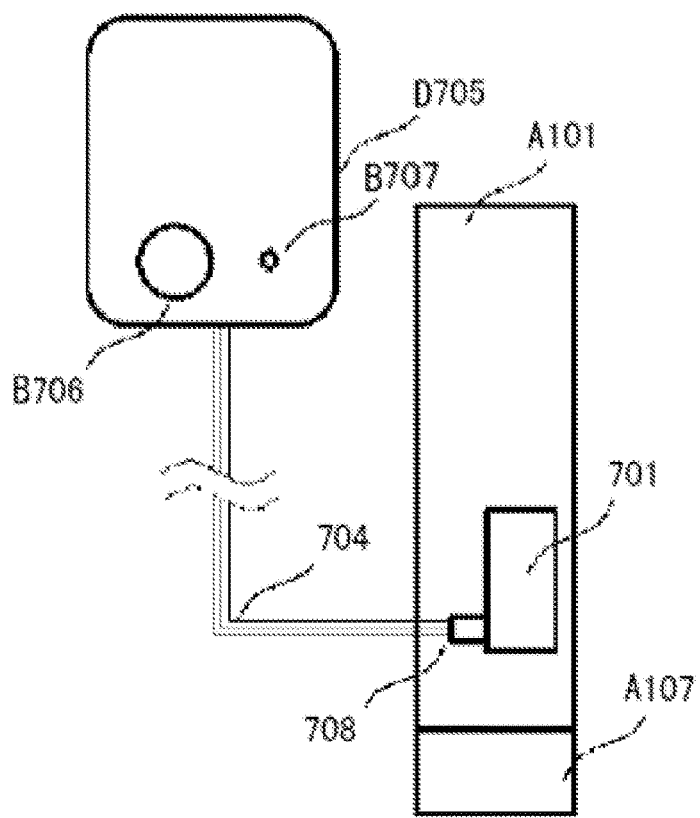

FIG. 7(a) shows a body D4 as another modified example. According to the body A1 and the body B2 as described above, various circuit parts installed in the controller A104 or the controller B404 are constituted to be arranged to the belt part A101, but without being limited thereto, they may be arranged to one other than the belt part A101. As shown in the figure, for example, it may be so constituted that a controller D705 is arranged as a separate body from the body D4. A view as seen from the direction of an arrow B in the same figure is shown in the same figure (b). The controller D705 is omitted in the same figure (a), but is described in the same figure (b). According to this case, it may be so constituted that the controller D705 as a separate body is put around one's neck with a neck strap, and is used; or is put in one's pocket, and is used. In this case, the controller D705 may be constituted so that an electric signal is able to be supplied to a wrist by an electrode A102 connected to a terminal part A702 and an electrode B103 connected to a terminal part B702, by being connected to the terminal part A702 and the terminal part B702 around a mount part 701 provided at a belt part A101 by a cable 704 and a connector 708. In addition, each terminal part and the electrodes are connected by a harness B709 inside the belt part A101. A switch B706 and LED-B707 are arranged in the controller D705, and are used similarly to the switch A105 and LED-A106, respectively.

Figure 9A:
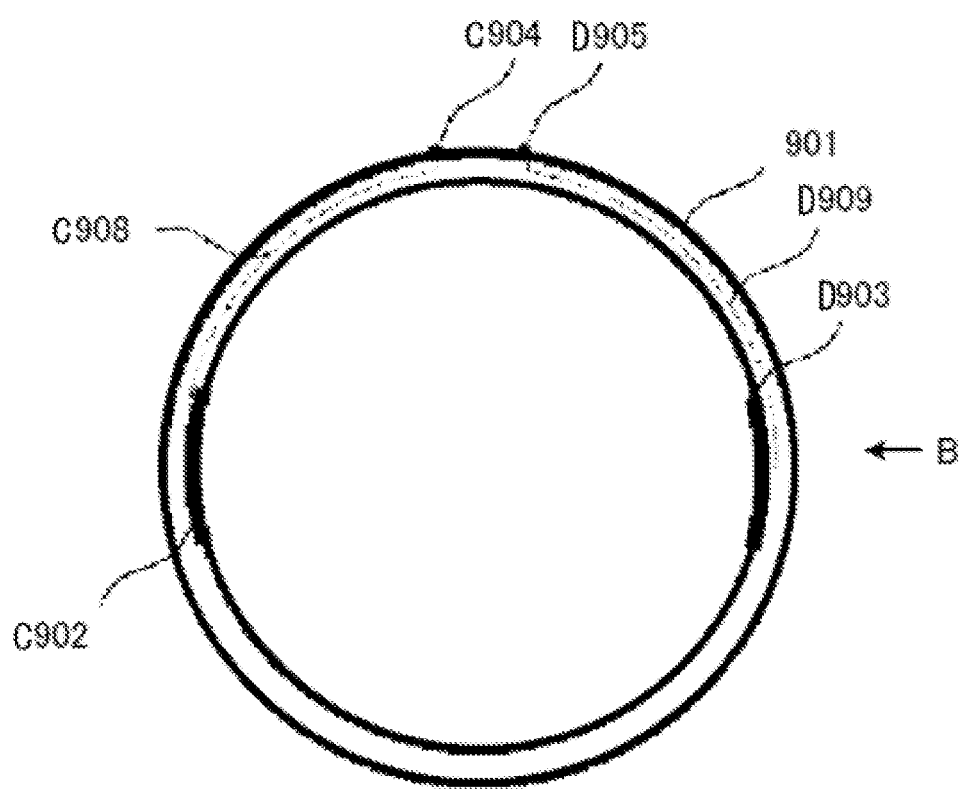
FIG. 9 is an explanatory diagram of another example according to the present invention.
Figure 9B:
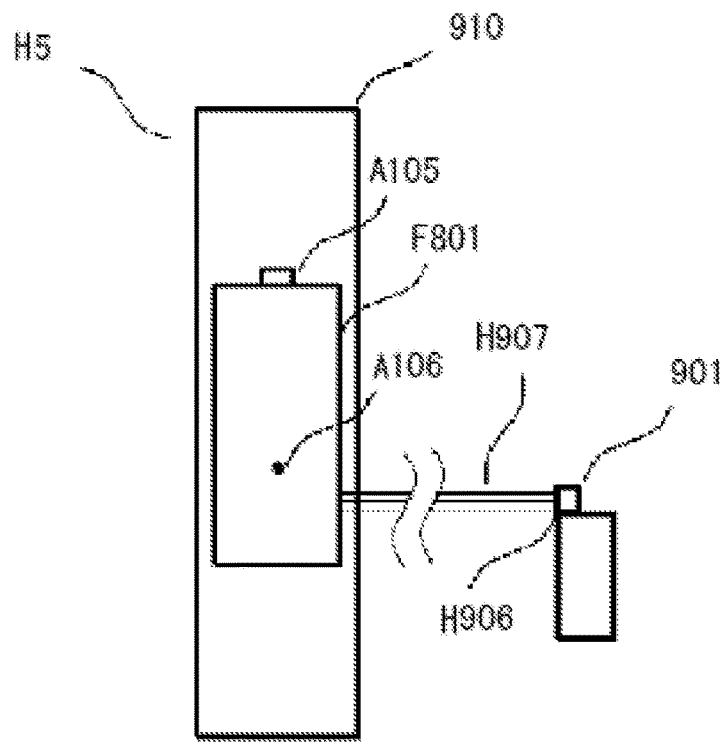
Figure 9C:
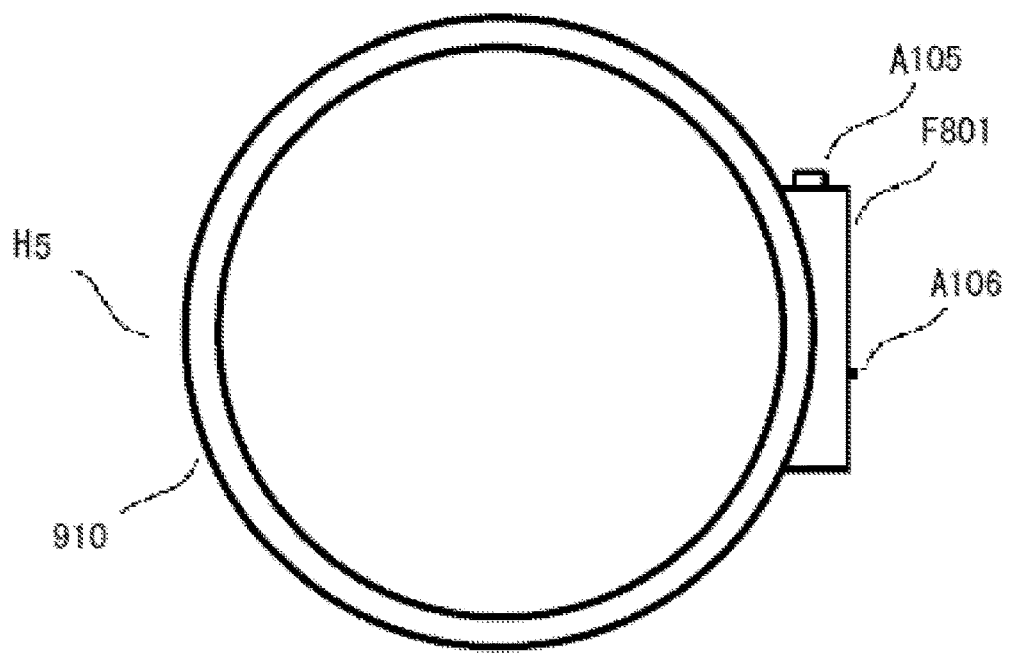
Figure 10A:
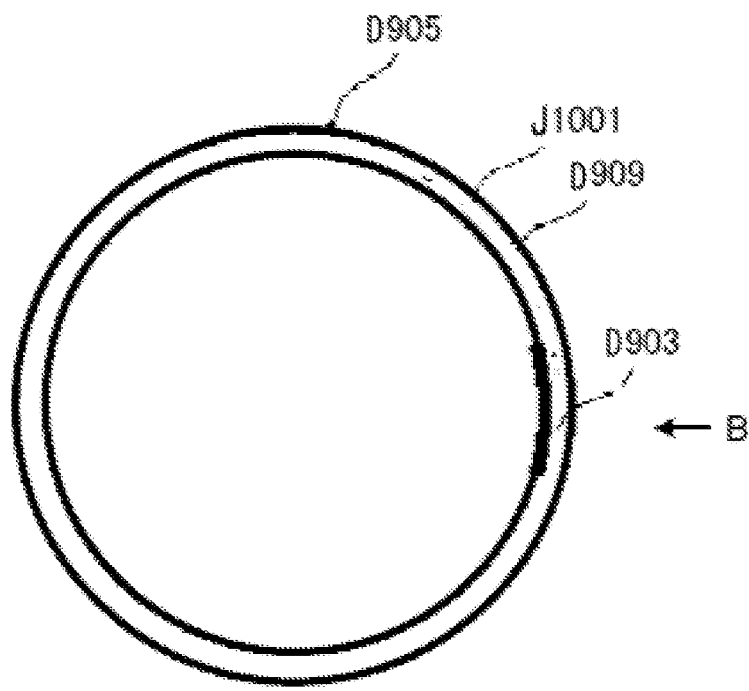
FIG. 10 is an explanatory diagram of another example according to the present invention.
Figure 10B:
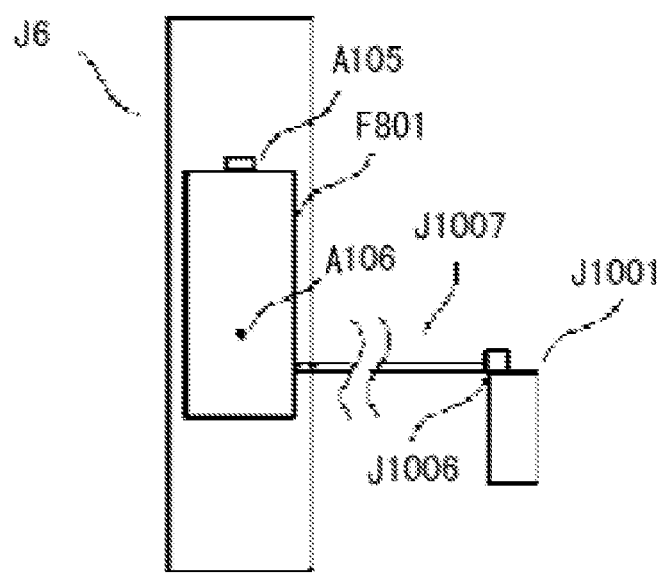
Figure 10C:
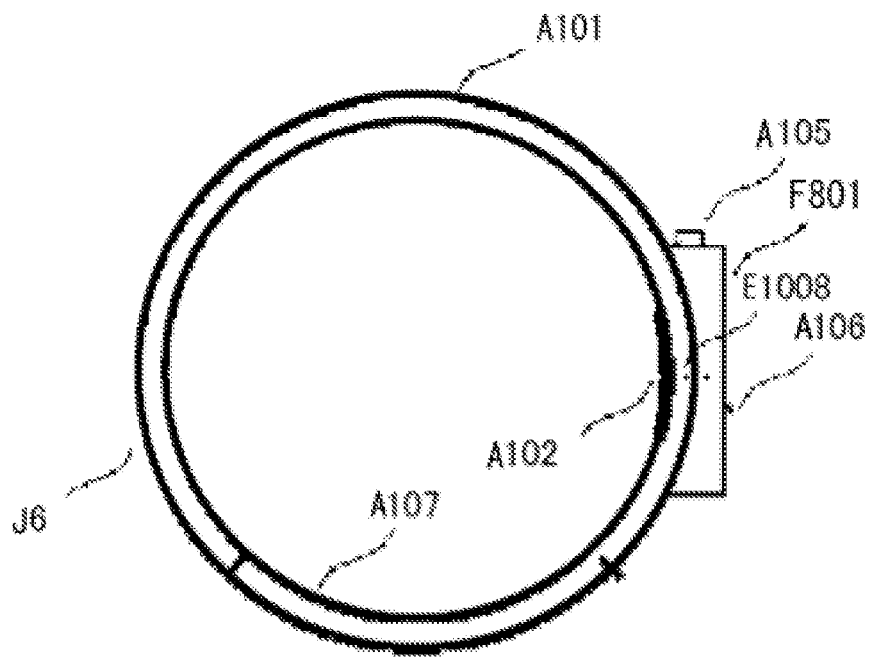
Figure 10D:
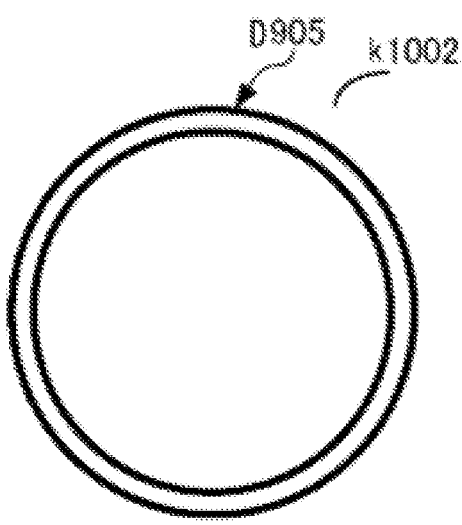

FIG. 9 shows a body H5 as another modified example. According to each example as described above, it is assumed to be worn around a wrist, but the present invention is not limited thereto, and for example, a finger-ring shape may be used. The case of having a ring 901 is shown as an example. An electrode C902 and an electrode D903 corresponding to the electrode A102 and the electrode B103, respectively are arranged; the electrode C902 is connected to a terminal part C904 via a harness C908; the electrode D903 is connected to a terminal part D905 via a harness D909; and the terminal part C904 and the terminal part D905 are connected to a cable H907 by a connector H906 to connect the ring 901 to the body H5 in which a controller is arranged. The controller may be any of controllers as described above; the same figure (b) shows the case where a controller F801 is used; the controller F801 is provided to the body H5 in a bracelet shape as shown in the same figure (c); and the body H5 is worn around a wrist and the ring 901 is worn and used like a finger-ring.

The ring 901 may be made of an insulating material such as a resin or the like, or may be made of rubber, silicone, or the like. The same figure is an outline drawing for explaining a configuration of each part, and thus the ring 901 in (a) and the body H5 in (c) are shown in the same size as each other, but it is not shown that both of them each have the same size.

FIG. 10 shows a modified example of FIG. 9. FIG. 9 shows a configuration in which 2 electrodes are arranged to the ring 901, but the present invention may exhibit a configuration of applying electric current to a distal portion of extremities or near the same, but is not limited thereto. Accordingly, for example, as shown in FIG. 10, it may be so constituted that only one of 2 electrodes used for feeding mild electric current is arranged to a ring J1001 in finger-ring shape, and another electrode is worn around another part, for example, a wrist. FIG. 10(a) shows a ring J1001 in a finger-ring shape similarly to FIG. 9(a). However, an electrode C902, a harness, and so forth each in FIG. 9(a) are not a ring J1001, and are arranged in a body J6 as an electrode A102 and a harness E1008, as shown in FIG. 10(c). The body J6 comprises the belt part A101 and the stretchable part A107, and this is the same configuration as in FIG. 1. An electrode D903 is connected to a terminal part D905 via a harness D909, and the terminal part D905 is connected to a cable J1007 by a connector J1006 and connected to a controller. The body J6 is worn around a wrist and the ring J1001 is worn and used like a finger-ring. The case of using an insulating material like the ring 901 is illustrated as an example for a configuration of the ring J1001, but without being limited thereto, a ring may be made to be like a ring k1002 in the same figure (d) by constituting it from for example, a conductor or a material exhibiting high conductivity such as platinum and silver and in this case, a more simple configuration is enabled since an electrode 903 and a harness D909 become unnecessary, and thus a ring K1002 can be used in place of the ring J1001 according to the same figure (b). The ring K1002 is connected to the body J6 by a harness E1007 and a terminal part D905.

Figure 11A:
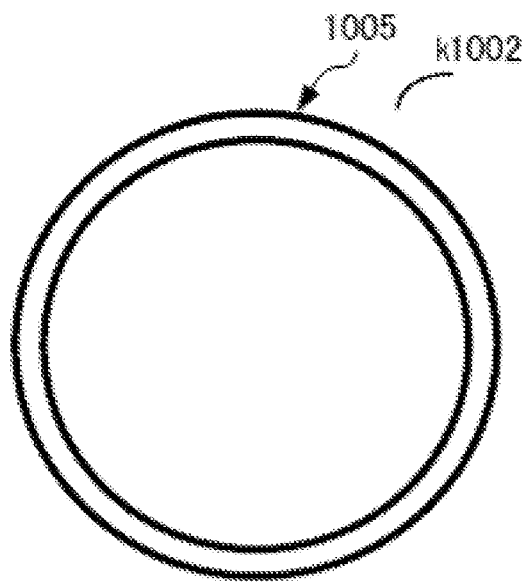
FIG. 11 is an explanatory diagram of another example according to the present invention.
Figure 11B:
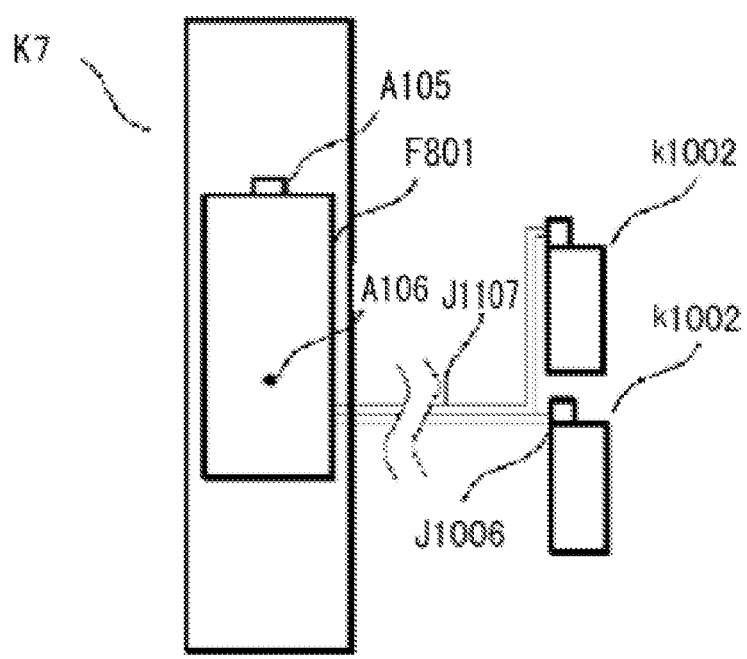
Figure 11C:
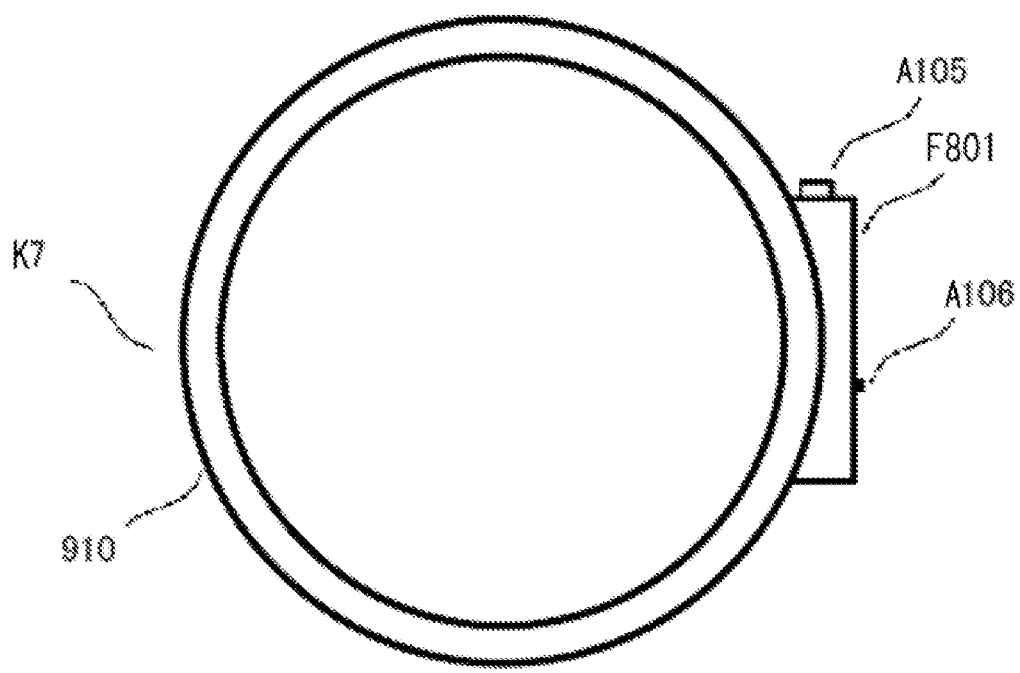

FIG. 11 shows another modified example. In the above-describe FIGS. 9 and 10, examples of using only one of the ring 901, the ring J1001, and the ring K1002 are shown, but the present invention is not limited thereto, for example, it may be so constituted that a plurality of rings K1002 are used. In FIG. 11, a configuration of using two rings K1002 is shown. In the present figure, a body K7 as a configuration in which a plurality of rings K1002 are usable is used in place of the body J6, and the two rings K1002 acting as electrodes are connected by a cable K1107.

Figure 12A:
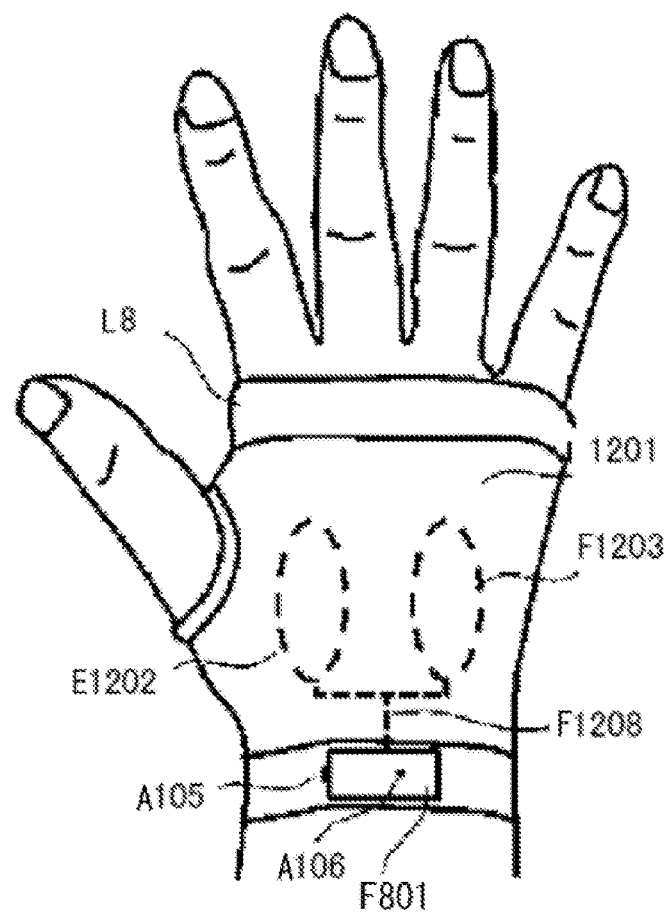
FIG. 12 is an explanatory diagram of another example according to the present invention.
Figures 12B, 12C:
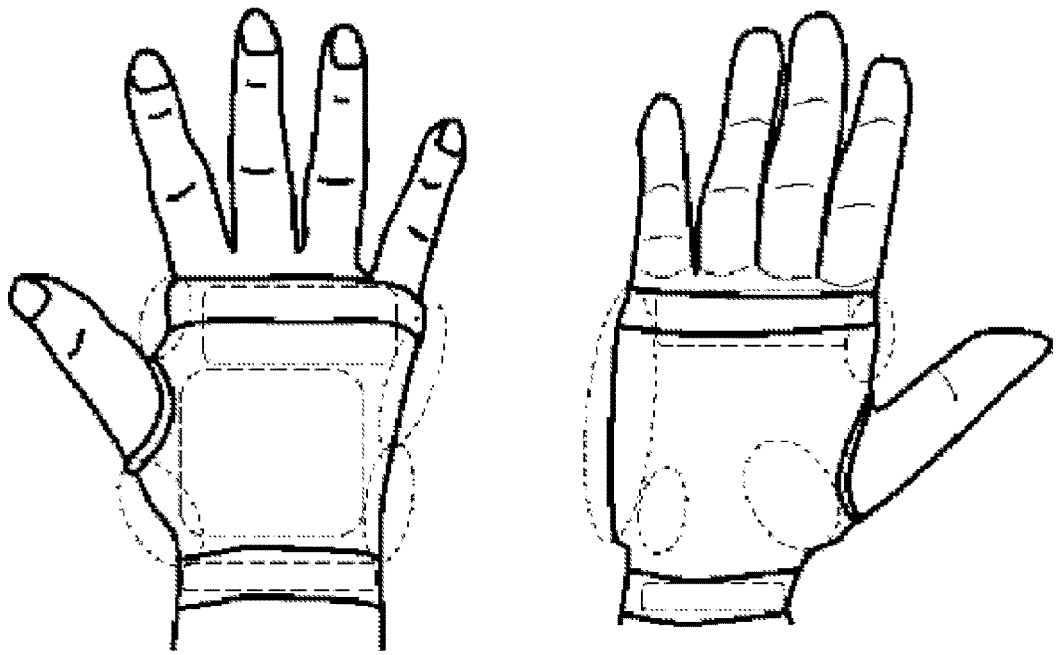

FIG. 12 shows another modified example. It is assumed to be worn around a wrist or a finger according to those described above, but the present invention is not limited thereto, for example, using as a supporter shape may be enabled, and a body L8 is shown as an example. The body L8 comprises a supporter 1201; an electrode E1202 and an electrode F1203 corresponding to the electrode A102 and the electrode B103, respectively are arranged; and the electrode E1202 and the electrode F1203 are connected to a controller via a harness F1208. In the figure, the electrode E1202 and the electrode F1203 are arranged so as to come into contact with the back of a hand, and cannot be directly seen from outside since the harness F1208 is also provided inside the supporter 1201, and thus their positions are shown with a dotted line. The controller may be any of the controllers as described above, and is used by wearing the body L8 as shown in FIG. 12, though in the same figure (a), the case of using a controller F801 is shown. The supporter 1201 may be made of an insulating material, for example, may be made of not only cloth such as cotton or the like, but also leather, rubber, silicone or the like.

In FIG. 12, the electrode E1202 and the electrode F1202 are arranged at the positions shown in the same figure (a), but the present invention is not limited thereto. According to positions where electrodes are arranged, in a plurality of areas enclosed with dotted lines in each of (b) and (c) of the same figure, the electrode is preferably able to be surely brought into contact with the skin, and when hereinafter, each of the areas where these electrodes are preferably arranged is referred to as an electrode area, two electrode areas are selected from these electrode areas to arrange respective electrodes one by one, or two electrodes are arranged in one area of these electrodes. For example, it may be so constituted that an electrode is arranged at a position of the root of a thumb, and at a position between the root of a little finger and a wrist. The same figure (b) shows electrode areas on the back side of a hand, and the same figure (c) shows electrode areas on the palm side of the hand.

Figure 13:
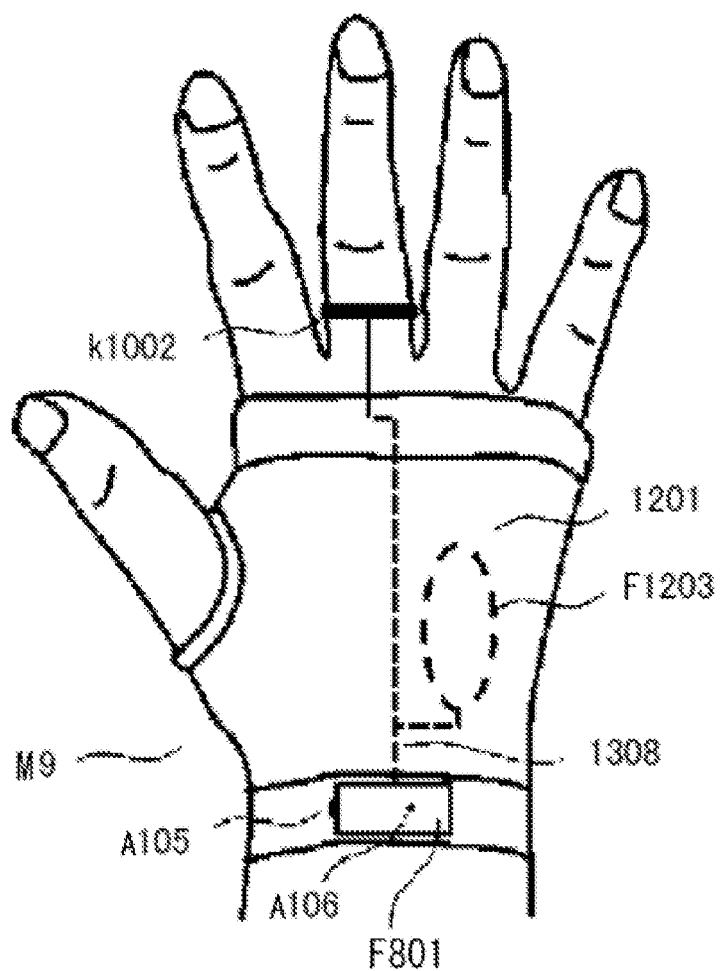
FIG. 13 is an explanatory diagram of another example according to the present invention.

FIG. 13 shows another modified example. FIG. 12 shows a configuration in which an electrode is arranged to a supporter 1201, but the present invention is not limited thereto, and a body M9 for which the ring J1001 or the ring K1002 are used as one of electrodes may be enabled and FIG. 13 shows the case of using the ring K1002 in place of the electrode E1202 in FIG. 12, but the ring K1002 may be used in place of the electrode F1203.

Figure 14:
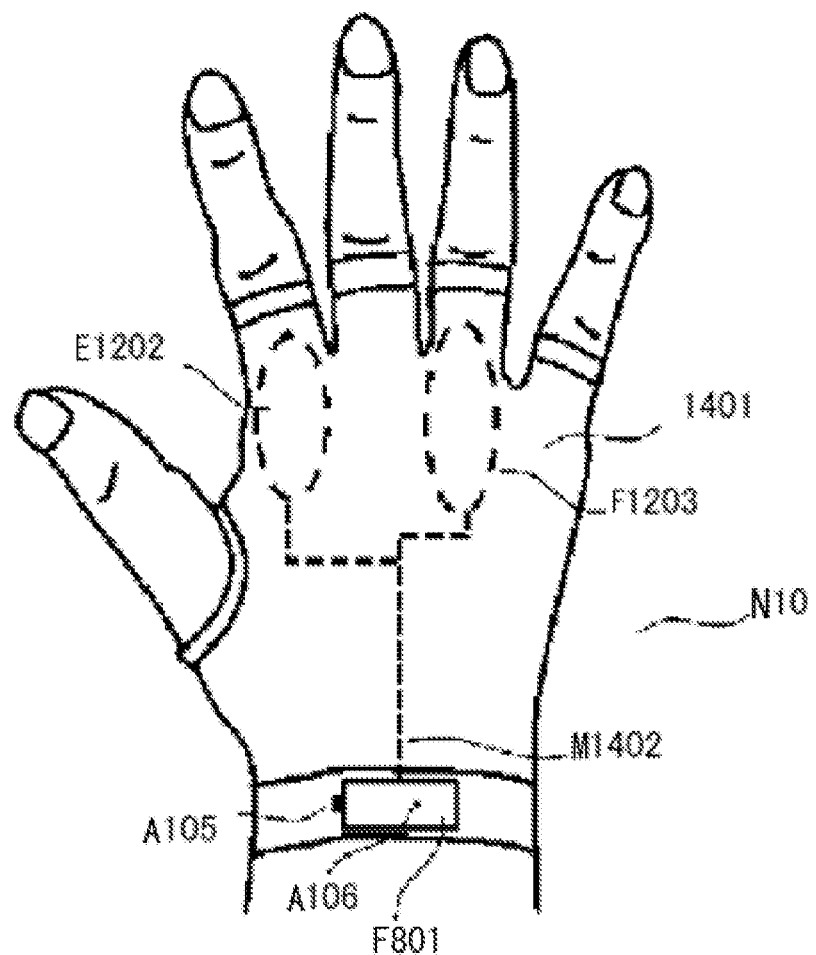
FIG. 14 is an explanatory diagram of another example according to the present invention.

FIG. 14 shows another modified example. Examples each of a supporter shape used for a wrist are shown in FIGS. 11 and 12, but the present invention is not limited thereto, and shows an example of a glove shape as shown in FIG. 14. It is assumed to be worn around a wrist and a finger according to those described above, but the present invention is not limited thereto, for example, the glove shape may be enabled, and a body N10 is shown as an example. The body N10 comprises a glove 1401; an electrode E1202 and an electrode F1203 corresponding to the electrode A102 and the electrode B103, respectively are arranged; and the electrode E1202 and the electrode F1203 are connected to a controller via a harness M1402. The controller may be any of the controller as described above; the same figure shows the case of using a controller F801; and the body N10 is worn and used as shown in the figure. A glove 1401 may be made of an insulating material similarly to the supporter 1201, but may be made of not only cloth such as cotton or the like, but also leather, rubber, silicone or the like. When using a body in a glove shape as shown in FIG. 14, the electrode area where the electrodes shown in FIG. 12 can be arranged spreads over to the surface of each finger covered by a glove, and though an electrode can be arranged around each finger, the ring 901 in a finger-ring shape, the ring J1001, and the ring K1002 are unnecessary, and thus it becomes easy to attach the electrodes thereto.

According to each of the above-described embodiments and modified examples, any of them shows an example of arranging a body as well as electrodes to a distal portion of extremities or near the same, for example, a wrist as well as a finger, but the present invention is not limited thereto. It may be so constituted that electrodes and a body are not worn around the distal portion of extremities or near the same, but are attached to a device with which a distal portion of a human body or a neighboring portion thereof is brought into contact. For example, electrodes and a body may be attached to a keyboard or a mouse when using a personal computer; a handle, an accelerator or a brake used when operating a bike or an automobile; and others such as a pen and a smartphone.

These are shown as an example in FIG. 15. The same figure (a) shows the case of being used for a mouse. A mouse 1501 comprising a body part 1504 with which a left-click 1502, a right-click 1503 and a palm are brought into contact may arrange an electrode G1505 and an electrode H1506 to the body part 1504. Any of the controllers may be used as a controller, for example, the controller F801 may be arranged to the body part 1504, and connected with the electrode G1505 and the electrode H1506. As to the electrode arrangement, electrodes may be arranged to a portion touched by a thumb, and a proximal end of the body part 1504, that is at a position with which a portion near a wrist of a palm comes into contact, as shown in the figure, and it may be so constituted that electric current follows through the thumb and the little finger with the electrode G1505 and the electrode H1506 arranged on the thumb side by placing the electrode G1505 on the right side face of the body part 1504 with which the little finger comes into contact. Alternatively, the electrode G1505 and the electrode H1506 may be arranged at the proximal end of the body part 1504.

It may be so constituted that the left-click 1502 or right-click 1503 in place of the electrode G1505 is formed from a conductive member, or electric current flows through a thumb, a forefinger and a middle finger by placing the electrode G1505 at the left-click 1502 or right-click 1503, and it may be so constituted that the above-described first signal current and the second signal are fed to a palm and a finger by the left-click 1502 or right-click 1503 and the electrode H1506 arranged at the body part 1504. It may be so constituted that the first signal and the second signal flow through the forefinger and the middle finger by arranging the electrode H1506 at the left-click 1502 or making at least a face of the left-click 1502 be a conductor, and arranging the electrode G1505 at the right-click 1503 or making at least a face of the right-click 1503 be a conductor. Further, a switch A105 and LED-A106 may be arranged as shown in the figure, for example.

Figure 15A:
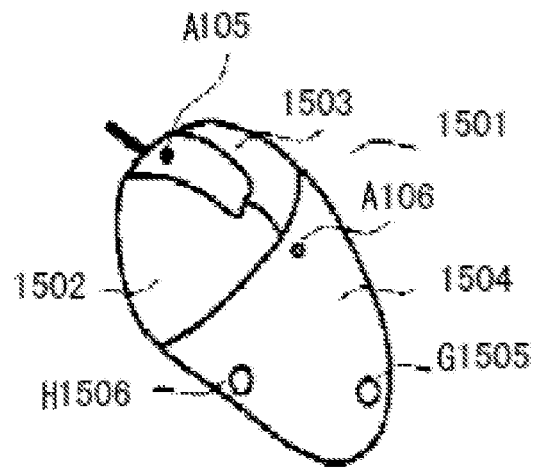
FIG. 15 is an explanatory diagram of another example according to the present invention.
Figure 15B:
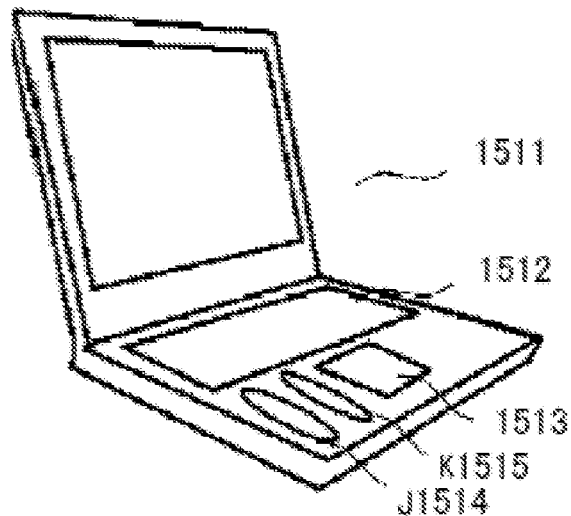

FIG. 15(b) shows an example of the case where a laptop computer is subjected to the present invention. As shown in the figure, the personal computer 1511 arranges an electrode J1514 and an electrode K1515 on the left side of a touch pad area 1513 where a mouse pointer is operated, in front of a keyboard area 1512; and is connected to a controller arranged inside the personal computer 1511. The controller may be any of the controllers as described above, for example, a controller F801 may be placed inside the personal computer 1511, and be connected with the electrode J1514 and the electrode K1515. In the figure, the electrodes are arranged on the left side of the touch pad area 1513, but without being limited thereto, it may be so constituted that they are arranged on the right side thereof, or are arranged on both sides of the touch pad area 1513 to feed the first signal current and the second signal as described above to each of palms of both hands. The electric signal fed via the electrode J1514 and the electrode K1515 may be controlled by applications installed inside the personal computer 1511.

Figure 15C:
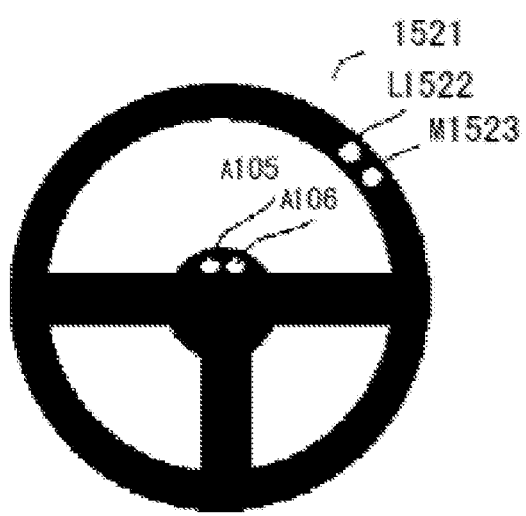

FIG. 15(c) shows an example of the case where a handle of an automobile is subjected to the present invention. As shown in the figure, an electrode L1522 and an electrode M1523 are arranged to a handle 1521, and are connected with a controller placed inside the handle 1521. Further, a switch A105 and LED-A106 may be arranged as shown in the figure, for example. The controller may any of the controllers as described above, for example, a controller F801 may be arranged to the handle 1521, and be connected with the electrode L1522 and the electrode M1523. The electrode L1522 and the electrode M1523 are provided on the right side of the handle, but the present invention is not limited thereto, and they may be provided on the left side, or on both sides thereof. Further, the electrode L1522 and the electrode M1523 are provided on the front side of the handle, but the present invention is not limited thereto, and even though they are provided on the side face, either one of them may be provided on the front side and the other may be provided on the side face.

Figure 15D:
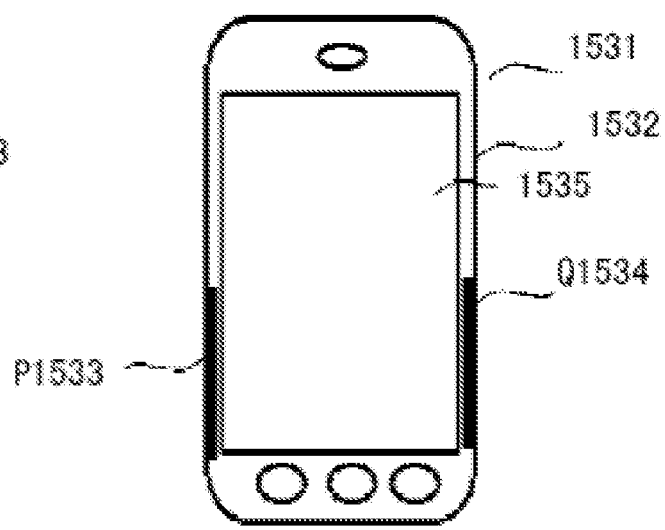

FIG. 15(d) shows an example of the case where a portable terminal is subjected to the present invention. As shown in the figure, an electrode P1533 and an electrode Q1534 are arranged on both sides of a housing 1532 or a display part 1535 of a smartphone 1531, and are connected with a controller placed inside the housing 1532. The controller may be any of the controllers as described above, for example, a controller F801 may be placed inside the housing 1532, and be connected with the electrode P1533 and the electrode Q1534. The electrode P1533 and the electrode Q1534 are arranged in the lower half parts on both sides of the housing 1532, but without being limited thereto, they may be arranged in the upper half parts, or on the upper and lower sides of either the right side or the left side. The electric signal fed via the electrode P1533 and the electrode Q1534 may be controlled by applications installed in the smartphone 1531.

According to the examples of FIG. 15, the controller and the electrode each may be provided as a separate body. For example, in the case of the mouse, the electric signal fed to extremities or neighboring portions thereof via the electrodes, using applications installed inside the personal computer may be controlled by arranging the controller in the personal computer to which the mouse is connected. In the case of the handle, it may be arranged not to a handle but to for example, an instrument panel or the like, and for example, the electric signal fed to a human body may be controlled by using a user interface for a car navigation system or the like.

In FIGS. 9 to 15, since mild and unfelt electric current is used as an electric signal to be fed, neither pain nor an unpleasant feeling is given to a user, and further, it is not felt that the electric current has been fed; and thus during for example, the user's operation or clerical work, or even though the user performs fine manual work, without at all being affected by the electric signal to be fed, these operations can be easily and non-forcedly continued even while feeding the electric signal without receiving any stress caused by the electric signal.

Further, the operations can be continued constantly while refreshing or relaxing by utilizing the first signal and the second signal, even during these operations, and thus not only work efficiency is improved, but a safe operation can be continued. For example, the operation can be performed constantly while refreshing by using the second signal when the operation takes a long time, or at night and the operation can performed while relaxing by the first signal during a traffic jam, and thus the safe operation can be continued. The operation is performed constantly while refreshing by using the second signal when the use of a personal computer takes a long time, or at night, or the work can be carried out while relaxing by the first signal, and thus the operation with no mistake can be non-forcedly performed.

According to each embodiment and each of various modified examples, the electric signal to be used utilizes a pulse group using rectangular waves, but the present invention is not limited thereto. For example, triangle waves may be used in place of the rectangular waves, and an impulse sequence using a plurality of impulses may be used, or sine waves may be used in place of the pulse group. Further, an electric signal having positive and negative amplitudes may be used, and unipolar waves having only positive or negative amplitude may be used. Alternatively, without limitation to the electric signal whose positive and negative amplitudes are equal to each other, used may be a waveform obtained by making the positive and negative amplitudes be different, changing forms of positive and negative waves, or being offset.

Another modified example is shown. According to each embodiment as described above, and modified examples thereof, it makes an applied electric signal be different to apply the electrical stimulation to a distal portion of extremities or near the same, for example, to a wrist or an ankle, and specifically, a different effect can be produced by lowering a frequency of pulses. According to this electric signal, for example, the second pulse group as schematically shown in FIG. 3(a) may be used, and the fourth pulse group as shown in FIG. 3(b) may be used. However, according to the present modified example to be used, the second pulse group is output as an electric signal to much lower a frequency to 5 Hz, for example. In this manner, used is another application different from the foregoing embodiments 1 and 2 by using an electric signal with a very low frequency (hereinafter, referred to as "ultralow frequency").

Figure 16:
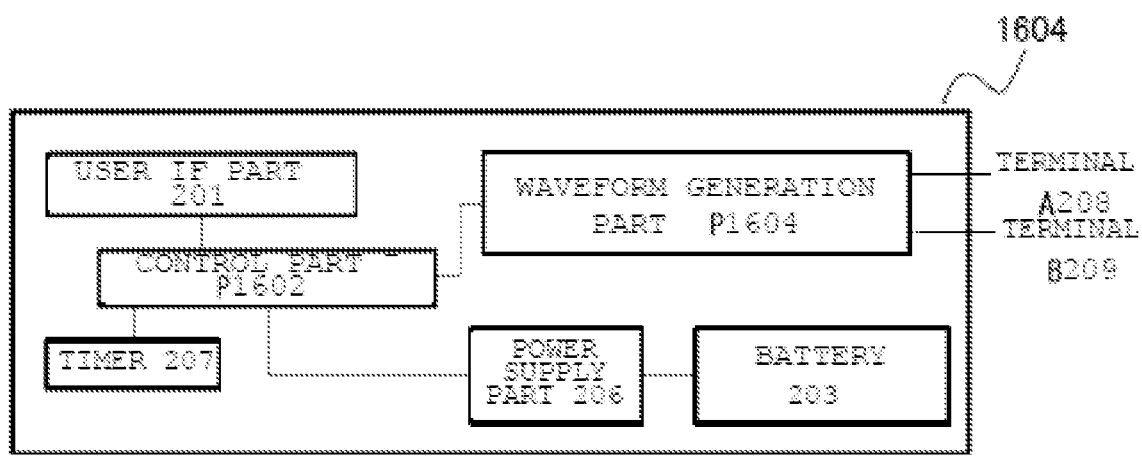
FIG. 16 is a block diagram of a controller according to the present invention.

As to a body P11 according to the present embodiment, the appearance may be identical to that of the body A1 or B2, and the explanation will be omitted. However, a controller P 1604 using a control part P1602 and a waveform generation part P1604 is used in the body P11 as shown in FIG. 16, for example.

The waveform generation part P1604 generates the second pulse group as being an amplitude of 50 µA by having an output electric signal at a frequency of 5 Hz. The effect to a whole body is produced by applying such an electrical stimulation, that is, a pulse group with an ultralow frequency of approximately 5 Hz to a distal portion of extremities or near the same. Specifically, the effect of normalizing autonomic nerves of the whole body can be expected. As described above, according to the present invention, no muscle contraction is generated, and thus the effect produced by the present invention has nothing to do with action caused by stimulation of specific muscles present in an electric current passage. According to the present invention, the effect of normalizing an autonomic balance via action on the autonomic nerves by applying the electrical stimulation to a distal portion of extremities or near the same can be expected, and is the effect specific to the present invention. Autonomic nerves in disorder cause various poor physical conditions as represented by for example, insomnia, sleepiness, tiredness, headache, dizziness and so forth. Expected is relief of allergy symptoms, and so forth, while improving these by normalizing the autonomic balance.

As a parameter of the second pulse group according to the present modified example, set is a frequency of 5 Hz, but the present invention is not limited thereto. A low frequency is preferred as an ultralow frequency at which it can be expected to improve the autonomic balance, and specifically, the effect starts to be produced by being set to 20 Hz or less. A frequency of 10 Hz or less becomes less in influence of the personal difference, and a frequency of 8 Hz or less highly tends to produce the most notable effect. Thus, the present embodiment uses 5 Hz as a frequency.

The lower the frequency of electrical stimulation to be used is, the better; for example, it appears that this may be DC. However, DC whose electric current flows continuously tends to make the electric current be easily concentrated due to lowering of conductivity, and to maintain the electric current concentration over a long period of time in cases where electrodes to be used are deteriorated; dirt, dust and impurities are generated or adhere; and so forth. It is not preferred that generation of the electric current concentration over a long period of time is likely to cause a malfunction such as a burn, discoloration, a blister or the like of skin, even when being mild as an electric current value of roughly 50 µA. Then, according to the present modified example, it can be avoided or reduced to continue the electric current concentration by applying not DC but an electric signal having an AC component thereto, and the above-described malfunction caused by the electric current concentration can be avoided.

A desirable frequency of the AC component is not always DC, that is, it is not always 0 Hz, for example, it is not preferred that a frequency of approximately 0.1 Hz highly tends to act substantially as DC, but a frequency of 0.5 Hz or more is preferable, and a frequency of 1 Hz or more is idealistic. Consequently, it appears that a frequency of 1 to 8 Hz is most preferable as an ultralow frequency, and according to the present embodiment, a frequency of 5 Hz is used as the ultralow frequency.

Any of the examples as described above is an example when used for a human body, but the present invention is applicable to another living body (hereinafter, referred to simply as "living body") other than a human body. Examples of living bodies may be living bodies kept in a zoo, such as for example, lions and giraffes and may be kept at home as a pet such as a dog, a cat, or the like, and the present invention is also applicable to livestock such as cattle, horses, pigs, chickens, goats and sheep. Herein, the livestock will be explained as an example. For example, the livestock is often reared inside a relatively narrow place, for example, inside a cow-house in the case of cattle, and thus influence is largely exerted on the growth and health state, quantity and quality of milk in the case of milk cows, and meat quality in the case of beef cattle by stress caused by factors of lack of exercise, being confined in the narrow place or others, or when tension caused by other factors continues for a long period of time.

Accordingly, it is made possible to improve milk quality and meat quality by releasing the stress and the tension via application of a device having been subjected to the present invention to a living body, for example, cattle. In this case, according to the device to be used, usable are a body A, a body B and these modified examples and so forth that are used in the above-described examples. However, a belt part A101 needs to be changed in size as well as in material quality for increasing strength so as to be usable around for example, a cattle ankle via adjustment to a living body.

Neither a large circuit configuration nor a battery is required particularly for the body as explained above, and thus no stress caused by size and weight thereof is felt by a living body. Not only new stress caused by being worn is immediately eliminated, but there is no feeing given by application of the electrical stimulation as well as no stress further caused by using the device having been subjected to the present invention, since no unfelt output as described above can be sensed by the living body as well.

However, since it bothers a living body that an unfamiliar device is attached thereto when initially being worn, cases where it licks or bites are assumed; and it appears that it is needed to cover switches with covers and to be designed so as to make a controller and a belt part be strong in strength, by assuming that the switches are unintentionally pushed or damaged. Alternatively, a configuration such that the switches are detached from the body part and remote control is wirelessly performed from outside is more preferable, since unintentional operations and damages caused when the living body licks or bites can be avoided.

When applying the device according to the present invention to the living body, there are some cases where applied electrodes, for example, the electrode A102 and the electrode B103 as described above are not suitable for use, with the situation as it is. Extremities of the living body are normally covered by body hairs, and thus no electric current is sufficiently fed. Accordingly, it is preferable that electric current from the electrode is designed to be sufficiently fed to the extremities by using for example, an elastic body exhibiting strong elasticity conductive rubber or conductive fibers without using electrodes each made of a conductive resin or metal as an electrode A102 and an electrode B103. Alternatively, the electric current may be designed to be sufficiently fed to the extremities of the living body by coating conductive gel exhibiting high viscosity on the surface of each of the electrode A102 and the electrode B103.

The following effect can be expected by applying the device according to the present invention to the living body. Not only each effect as provided below can be singly expected, but a plurality of effects can be simultaneously expected. One of the effects is relief in tension. The reason for tension is not limited to a specific reason, for example, provided is tension produced due to stress caused by being confined inside a narrow cage or a room. In addition, there are stress caused by weather such as unusual low temperature, high temperatures or the like, typhoon, strong wind, long rain, or dry weather; and tension caused by cautiousness generated from construction work carried out in the neighborhood, and so forth. Alternatively, there is also provided tension caused by a physical condition changed due to poor health, pregnancy or the like.

The tension of a living body is relaxed with relief from stress by feeding the first signal to extremities of the living body using a body A1, a body E or a body F for tension relaxation as described above, or a device having a function capable of outputting pulses, equivalent to the foregoing; thereby being usable for physical condition maintenance and management of the living body such as maintenance and improvement of a health state of the living body or the like.

Alternatively, it is effective to feed the first signal of each of them to the extremities of the living body by predicting generation of the tension, or in advance for an individual body that gets nervous easily. Further, as to an individual body of overactivity, it is also effective to suppress the activity by feeding the first signal thereto. As an example, the effect of accelerating healing of injury and illness can also be expected by feeding the first signal to injured and sick individual bodies to suppress the activity.

Another effect can be expected by using the device according to the present invention for the living body. The other effect means to promote the activity. For example, an aged living body that is to be made to lower the activity itself lacks in exercise, thereby inducing declines of muscles caused by lack of exercise, joint disorders, and an internal disease. According to living bodies in a zoo as well, their activities in a cage are limited, and feed is able to be easily obtained in a periodical manner, and thus exercise opportunity is reduced, resulting in lack of exercise. When lacking in exercise, possibility of inducing injury and illness becomes high. Accordingly, a refreshed feeling is given to a living body to enhance the activity and activation of the living body, and to eliminate lack of exercise by feeding the second signal to extremities of the living body using a body B2, a body E or a body F, or a device having a function capable of outputting pulses, equivalent to the foregoing; thereby being usable for the physical condition maintenance and management of the living body. In the case of cattle, pigs, goats, sheep or the like, maintenance/management of meat quality, and improvement and maintenance/management of milk quality and milk amount also become possible. It is made possible to prevent injury and illness even when being aged, by feeding the second signal to the living body whose activation and activity have been lowered to raise the activation, for example, by preventing muscles of the aged living body from being lowered to maintain the strong muscles, or by improving lack of exercise, thereby being able to maintain health.

Not only the health management of a living body is performed with a device according to the present invention by using the first signal and the second signal, but the quality control can be carried out in the case of livestock. For example, it is also possible that an activity amount of beef cattle is increased by applying the second signal to the beef cattle to increase a ratio of so-called read meat, or the activity amount of the beef cattle is restricted by frequently applying the first signal thereto to adjust hardness and lipid of the meat and control meat quality, for example, a ratio of so-called marbled fat for keeping soft meat quality is made large and is controlled. In this case, no stress is given to the livestock at all, since exercise of the livestock is not forcibly limited, nor the exercise is forced.

EXPLANATION OF THE SYMBOLS

1 Body A
2 Body B
3 Body C
4 Body D
5 Body H
6 Body J
7 Body K
8 Body L
9 Body M
10 Body N
11 Body P
101 Belt A 102 Electrode A
103 Electrode B
104 Controller A
105 Switch A
106 LED-A
107 Stretchable part A
108 Harness A
201 User IF part
202 Control part A
203 Battery
204 Waveform generation part A
206 Power supply part
207 Timer
208 Terminal A
209 Terminal B
404 Controller B
504 Waveform generation part B
701 Mount part
702 Terminal part A
703 Terminal part B
704 Cable
705 Controller D
706 Switch B
707 LED-B
708 Connector
709 Harness B
801 Controller F
802 Control part F
804 Waveform generation part F
901 Ring
902 Electrode C
903 Electrode D
904 Terminal part C
905 Terminal part D
906 Connector H
907 Cable H
908 Harness C
909 Harness D
1001 Ring J
1002 Ring K
1006 Connector J
1007 Cable J
1008 Harness E
1107 Cable K
1201 Supporter
1202 Electrode E
1203 Electrode F
1208 Harness F
1401 Glove
1402 Harness M
1501 Mouse
1502 Left-click
1503 Right-click
1504 Body part
1505 Electrode G
1506 Electrode H
1511 Personal computer
1512 Keyboard area
1513 Touch pad area
1514 Electrode J
1515 Electrode K
1521 Handle
1522 Electrode L
1523 Electrode M
1531 Smartphone
1532 Housing
1533 Electrode P
1534 Electrode Q
1535 Display part
1602 Control part P
1604 Controller P

The invention claimed is:

1. A current stimulation device comprising:
a main body;
a first electrode;
a second electrode;
an output circuitry arranged in the main body; and
a controller configured to control the output circuitry, wherein
the output circuitry is configured to output or supply a first electric signal or a second electric signal as a selected electrical signal, wherein the selected electrical signal having an amplitude less than 20 mA, wherein
the selected electrical signal being a sequence of electric signals,
the sequence of electric signals being formed consisting of at least a first pulse group, a second pulse group and a third pulse group,
the first pulse group being a first pulse train including at least a first pulse with a first amplitude, and a pulse output after the first pulse with an amplitude larger than the first amplitude,
the second pulse group being a second pulse train including a plurality of pulses with a second amplitude, and
the third pulse group being a third pulse train including at least a third pulse with a third amplitude and a subsequent pulse output after the third pulse with an amplitude smaller than the third amplitude,
the first electric signal is configured to be applied to a distal portion of extremities, and
the second electric signal is configured to be applied to the distal portion of extremities,
wherein the main body includes a switch,
wherein the selected signal is started in the case where the switch is pressed once, and
wherein the selected signal is started in the case where the switch is pressed to select either the first electric signal or the second electric signal and in a different manner than the switched being pressed once,
if the first electric signal is selected only by the pressing the switch, then the output circuitry is configured to set a first duration of the first pulse train belonging to the sequence of the electric signals less than one second automatically by the controller based on a user's selection of the first signal and configured to output/apply the sequence of the electric signals with the first duration of the first pulse train set less than one second as the first electric signal,
the first duration of the first pulse train belonging to the sequence of the electric signals being formed consisting of at least the first pulse group, the second pulse group and the third pulse group,
if the second electric signal is selected only by the pressing the switch, then the output circuitry is configured to set the first duration of the first pulse train belonging to the sequence of the electric signals more than one second automatically by the controller based on the user'selection of the second signal and configured to output/apply the sequence of the electric signals with the first duration of the first pulse train set more than one second as the second electric signal, the first duration of the first pulse train belonging to the sequence of the electric signals being formed consisting of at least the first pulse group, the second pulse group and the third pulse group, the first duration is required for outputting all pulses in the first pulse train, the output circuitry is further configured to output the first pulse train starting at a beginning of the first duration, the output circuitry is further configured to output said all pulses in the first pulse train finishing at an end of the first duration, the output circuitry is further configured to output a final pulse in the first pulse train finishing at an end of the first duration, the output circuitry is further configured to output the first pulse with the first amplitude in the first pulse train at said beginning of the first duration, and an amplitude of a pulse at said end of the first duration is larger than the first amplitude.

2. The current stimulation device according to claim 1, wherein the main body has a ring-shaped portion, the first electrode and the second electrode are arranged on an inside surface of the ring-shaped portion, the inside surface is configured to contact with a distal portion or around the distal portion of extremities, and both of the first electrode and the second electrode are configured to contact with the distal portion or around the distal portion of extremities directly to apply the selected electrical signal to the distal portion or around the distal portion of extremities.

3. The current stimulation device according to claim 1, wherein the main body has a ring-shaped portion.

4. The current stimulation device according to claim 1, wherein the main body has a ring-shaped portion, and the first electrode and the second electrode are arranged on an inside surface of the ring-shaped portion.

5. The current stimulation device according to claim 1, wherein the first electrode and the second electrode are arranged on an inside surface of the main body.

6. The current stimulation device according to claim 1, wherein the main body has a ring-shaped portion, the first electrode and the second electrode are arranged on an inside surface of the ring-shaped portion, and the inside surface is configured to contact with a distal portion or around the distal portion of extremities.

7. The current stimulation device according to claim 1, wherein the first electrode and the second electrode are arranged on an inside surface of the main body, and the inside surface is configured to contact with a distal portion or around the distal portion of extremities.

8. The current stimulation device according to claim 1, wherein the first electrode and the second electrode are arranged on an inside surface of the main body, the inside surface is configured to contact with a distal portion or around the distal portion of extremities, and both of the first electrode and the second electrode are configured to contact with the distal portion or around the distal portion of extremities directly to apply the selected electrical signal to the distal portion or around the distal portion of extremities.

\* \* \* \* \*